United States Patent
Van Engelen et al.

(10) Patent No.: US 9,862,916 B2
(45) Date of Patent: *Jan. 9, 2018

(54) STRUCTURING AGENT FOR LIQUID DETERGENT AND PERSONAL CARE PRODUCTS

(71) Applicant: Koninklijke Coöperatie Cosun U.A., Breda (NL)

(72) Inventors: Gerardus Petrus Franciscus Maria Van Engelen, Bavel (NL); Gijsbert Adriaan Van Ingen, Breda (NL); Corne Meeuwissen, Breda (NL); Robert Nolles, 's-Hertogenbosch (NL)

(73) Assignee: Koninklijke Coöperatie Cosun U.A., Breda (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/417,501

(22) PCT Filed: Jul. 26, 2013

(86) PCT No.: PCT/NL2013/050560
§ 371 (c)(1),
(2) Date: Jan. 26, 2015

(87) PCT Pub. No.: WO2014/017913
PCT Pub. Date: Jan. 30, 2014

(65) Prior Publication Data
US 2015/0210967 A1    Jul. 30, 2015

(30) Foreign Application Priority Data

Jul. 27, 2012  (EP) .................................... 12178190
Apr. 22, 2013  (EP) .................................... 13164717

(51) Int. Cl.
*C11D 1/00* (2006.01)
*C11D 3/382* (2006.01)
(Continued)

(52) U.S. Cl.
CPC .......... *C11D 17/0026* (2013.01); *A61K 8/731* (2013.01); *A61Q 5/02* (2013.01);
(Continued)

(58) Field of Classification Search
CPC ........... C11D 1/00; C11D 3/222; C11D 3/382; C11D 7/44; C11D 17/0026
See application file for complete search history.

(56) References Cited

U.S. PATENT DOCUMENTS

| 4,374,702 A | 2/1983 | Turbak et al. |
| 4,378,381 A | 3/1983 | Turbak et al. |

(Continued)

FOREIGN PATENT DOCUMENTS

| EP | 0 102 829 | 3/1984 |
| EP | 0 134 084 | 3/1985 |

(Continued)

OTHER PUBLICATIONS

Dinand et al., "Parenchymal cell cellulose from sugar beet pulp: preparation and properties", Cellulose, 1996, vol. 3, pp. 183-188.
(Continued)

*Primary Examiner* — Brian P Mruk
(74) *Attorney, Agent, or Firm* — Gilberto M. Villacorta; Sunit Talapatra; Foley & Lardner LLP

(57) ABSTRACT

This invention relates to an external structuring agent for application in liquid detergent and personal care products. It has been found that cellulose based particles, which comprise cell wall material and their networks of cellulose based fibers and nanofibrils can advantageously be used to structure liquid detergent and personal care products, providing (Continued)

certain benefits that are much sought after in the design of such products. It is assumed that the organization of the cellulose fibrils, as it exists in the parenchymal cell walls, is at least partly retained in the cellulose based particles of the invention, even though part of the pectin and hemicellulose is removed there from. The process of making the structuring agent involves processing under relatively mild conditions, of a biological material that is currently considered a by-product.

23 Claims, 8 Drawing Sheets

(51) Int. Cl.
| | | |
|---|---|---|
| *C11D 7/44* | (2006.01) | |
| *C11D 17/00* | (2006.01) | |
| *C08H 8/00* | (2010.01) | |
| *C11D 3/22* | (2006.01) | |
| *C08L 1/02* | (2006.01) | |
| *D21C 5/00* | (2006.01) | |
| *D21H 11/12* | (2006.01) | |
| *A61K 8/73* | (2006.01) | |
| *A61Q 5/02* | (2006.01) | |
| *A61Q 5/12* | (2006.01) | |
| *A61Q 19/10* | (2006.01) | |

(52) U.S. Cl.
CPC .............. *A61Q 5/12* (2013.01); *A61Q 19/10* (2013.01); *C08H 8/00* (2013.01); *C08L 1/02* (2013.01); *C11D 3/222* (2013.01); *C11D 3/382* (2013.01); *C11D 7/44* (2013.01); *D21C 5/00* (2013.01); *D21H 11/12* (2013.01); *C08L 2205/16* (2013.01); *C08L 2205/18* (2013.01); *Y10T 428/2982* (2015.01)

(56) References Cited

U.S. PATENT DOCUMENTS

| | | | |
|---|---|---|---|
| 4,629,575 A | 12/1986 | Weibel | |
| 4,831,127 A | 5/1989 | Weibel | |
| 4,923,981 A | 5/1990 | Weibel et al. | |
| 5,179,076 A | 1/1993 | Elward-Berry | |
| 5,252,352 A | 10/1993 | Banach et al. | |
| 5,276,075 A | 1/1994 | Santini | |
| 5,567,462 A | 10/1996 | Ehrlich | |
| 5,656,734 A | 8/1997 | Ehrlich | |
| 5,964,983 A | 10/1999 | Dinand et al. | |
| 5,998,349 A * | 12/1999 | Guillou ................ | C11D 3/042 510/249 |
| 6,103,790 A | 8/2000 | Cavaille et al. | |
| 6,117,545 A | 9/2000 | Cavaille et al. | |
| 6,129,867 A | 10/2000 | Chevalier et al. | |
| 6,312,669 B1 | 11/2001 | Cantiani et al. | |
| 6,348,436 B1 | 2/2002 | Langlois et al. | |
| 6,703,497 B1 | 3/2004 | Ladouce et al. | |
| 6,967,027 B1 | 11/2005 | Heux et al. | |
| 7,705,084 B2 | 4/2010 | Van De Mark et al. | |
| 7,776,807 B2 | 8/2010 | Canto et al. | |
| 8,153,707 B2 | 4/2012 | Lynch et al. | |
| 2004/0086626 A1 | 5/2004 | Lundberg et al. | |
| 2005/0074542 A1 | 4/2005 | Lundberg et al. | |
| 2005/0256262 A1 | 11/2005 | Hill et al. | |
| 2006/0102869 A1 | 5/2006 | Cavaille et al. | |
| 2006/0289132 A1 | 12/2006 | Heijnesson-Hulten | |
| 2008/0108541 A1 | 5/2008 | Swazey | |
| 2008/0146485 A1 | 6/2008 | Swazey | |
| 2008/0146701 A1 | 6/2008 | Sain et al. | |
| 2009/0269376 A1 | 10/2009 | Lundberg et al. | |
| 2012/0142909 A1 | 6/2012 | Lundberg | |
| 2014/0124150 A1 | 5/2014 | Sabourin et al. | |
| 2015/0203737 A1 | 7/2015 | Van Engelen et al. | |
| 2015/0210957 A1* | 7/2015 | Napolitano .............. | C11D 1/83 510/424 |

FOREIGN PATENT DOCUMENTS

| | | |
|---|---|---|
| JP | 2008-179666 A | 8/2008 |
| WO | WO-2009/101545 | 8/2009 |
| WO | WO-2010/105847 A1 | 9/2010 |
| WO | WO-2012/003307 A2 | 1/2012 |
| WO | WO-2012/052306 A1 | 4/2012 |
| WO | WO-2012/065924 | 5/2012 |
| WO | WO-2012/065925 | 5/2012 |

OTHER PUBLICATIONS

European Search Report of EP Application No. 12178190 dated Nov. 26, 2012.
International Search Report of PCT/NL2013/050558 dated Aug. 29, 2013.
International Search Report of PCT/NL2013/050559 dated Oct. 21, 2013.
International Search Report of PCT/NL2013/050560 dated Oct. 15, 2013.
Machine Translation of JP 2008-179666, filed Aug. 7, 2008.
U.S. Appl. No. 14/417,505, filed Jan. 26, 2015.
U.S. Appl. No. 14/417,513, filed Jan. 26, 2015.

* cited by examiner

STRUCTURING AGENT FOR LIQUID DETERGENT AND PERSONAL CARE PRODUCTS

CROSS-REFERENCE TO RELATED APPLICATIONS

This application is the National Phase of International Patent Application No. PCT/NL2013/050560, filed Jul. 26, 2013, published as WO 2014/017913, which claims priority to European Application No. 12178190.0, filed Jul. 27, 2012, and European Application No. 13164717.4, filed Apr. 22, 2013. The contents of these applications are herein incorporated by reference in their entirety.

FIELD OF THE INVENTION

This invention relates to structuring agents for liquid detergent and personal care products.

BACKGROUND OF THE INVENTION

Liquid detergent products present a challenge to formulators when it comes to structuring the compositions. One particular purpose of providing distinctive structure is to provide specific flow behavior. Specific types of applications often require specific flow behavior. Another common purpose of providing structure is to enable suspending solid particles in the detergent matrix, or dispersing liquids which are immiscible in the detergent matrix. In non-structured liquid detergent or personal care products, the presence of such ingredients generally leads to sedimentation or phase separation and therefore renders such detergents unacceptable from a consumer's viewpoint.

Hence, two structuring properties are typically desired in liquid detergent and personal care products: shear thinning capabilities and bead and/or particle suspension capabilities. The capability to suspend particles in principle is characterized by the yield stress value. High zero-shear viscosity values may also be indicative of particle suspension capability. Shear thinning capabilities are typically characterized by the pouring viscosity and the ratio of the pouring viscosity and low-stress viscosity values. As will be understood, the ability of a certain structuring agent to provide shear thinning capabilities alone is insufficient to determine whether the liquid product is capable of suspending bead particles with sufficient stability and vice versa.

Structuring benefits are desired at as low a level of external structurant as possible for cost and formulation concerns. For example, excessive amounts of external structuring agent may provide the particle suspension capability but result in the liquid composition becoming overly viscous and non-pourable.

It is also relevant that a structuring agent can be applied in highly concentrated liquid detergent compositions, which have low dosage volumes with high cleaning performance. Many attempts have been and still are made to produce concentrated products containing less than 50% water and high active ingredient levels. These low dosage concentrated products are in high demand since they conserve resources and can be sold in small packages. The stabilization of liquid detergent products containing very high levels of surfactants and other active ingredients and lower levels of water has proven to be particularly challenging.

A further relevant trend seen in the field of liquid detergent products is the increasing demand for bio-based products, to reduce the environmental impact of the products.

Conventional approaches for providing distinctive structure to liquid detergent and personal care products include the addition of specific structuring agents, including both internal and external structuring agents. Examples of known internal structuring agents include: surfactants and electrolytes. External structuring agents include polymers or gums, many of which are known to swell or expand when hydrated to form random dispersion of independent microgel particles. Examples include acrylate polymers, structuring gums (e.g., xanthan gum), starch, agar, hydroxyl alkyl cellulose etc. Although gums have been used to provide structuring benefits, the gums are pH dependant, i.e. failing at pH above 10. The stability of gums is also unsatisfactory at high electrolyte concentrations. Further, certain gums have been found to be susceptible to degradation in the presence of detersive enzymes. Thus, there remains a need for other external structuring agents less susceptible to these and other known problems. When large particles are suspended (e.g., polyethylene particles, guar beads), levels of polymer used is typically 1% or more.

It has previously been shown that when certain fibrous polymers (e.g., micro fibrous cellulose with large aspect ratios) are used as structurants, these may provide efficient suspending properties even at polymer levels as low as 0.1% (see e.g. U.S. Pat. No. 7,776,807, US2008/0108541 and US2008/0146485). The fibrous polymers are believed to form spider-network like structures which efficiently trap the particles inside the network and thereby impart good suspending properties. The polymers are said to provide excellent rheological properties and are said to be salt tolerant if salt is used in the formulation.

Another material reported to provide structuring benefits is bacterial cellulose. Bacterial cellulose is typically cultured using a bacterial strain of *Acetobacter aceti* var. *xylinum* and dried using spray drying or freeze drying techniques. Attempts to manufacture and prepare the dried bacterial cellulose compositions which can be rehydrated and activated into a particulate cellulose material for use in end products are known.

WO2009101545 describes an external structuring agent for use in liquid detergent products that comprises a bacterial cellulose network. This external structuring agent is said to provide both shear thinning capabilities and particle suspension capabilities.

According to WO2012/065924 and WO2012/065925 external structuring agents based on micro fibrous cellulose, such as in particular bacterial cellulose, have a zero or near zero stress-shear rate profile (i.e., zero stress-shear rate slope when plotting shear rate versus stress), resulting in flow instability and shear banding. According to WO2012/065924 these flow instability problems can be reduced or eliminated by the addition of low molecular weight water soluble polymers to the compositions comprising microfibrous (bacterial) cellulose. WO2012/065925 teaches to overcome the flow instability problems by the addition of citrus fibre to the compositions comprising microfibrous (bacterial) cellulose as an external structuring agent. The citrus fibre according to WO2012/065925 is obtained by extraction of peels and vesicles in the pulp of citrus fruit that remains after removal of the sugars to leave mainly insoluble hemicellulose.

Apart from the flow instability problems bacterial cellulose also has the obvious disadvantage that it is a relatively expensive material.

WO2012/052306 concerns laundry detergent products containing enzymes with cellulase activity. WO2012/052306 teaches to employ citrus fibre as an external structurant because it can be employed at much higher levels than bacterial MFC due to its lower cost and lower efficacy as a structurant, which is said to confer the advantage of greater resistance to destabilisation under the influence of cellulase. At a level of 0.12% the citrus fibre material did not provide sufficient susepension capability. WO2012/052306 furthermore does not address the issue of flow instability and shear banding.

To date, no liquid detergent or personal care products containing any of these types of cellulose materials as external structuring agent have become available commercially. This may be cost-related and/or the consequence of certain shortcomings of these materials in practice, e.g. in relation to performance, stability, etc.

There still remains a need for an external structuring agent which provides shear thinning capabilities and sufficient stability and particle suspension capabilities in liquid detergent and personal care products while avoiding one or more of the above mentioned problems encountered with prior art formulations.

SUMMARY OF THE INVENTION

The inventors have developed parenchymal cellulose based particles, which comprise cell wall material and their networks of cellulose based fibers and nanofibrils, which can advantageously be used as an external structuring agent in liquid detergent and personal care products. The particulate parenchymal cellose material of this invention, in particular, delivers relatively high viscosity at low dosage levels, is shear thinning and has a relatively high yield stress. Moreover, the particulate parenchymal cellose material of this invention provides stable structuring properties over a broad temperature range, a broad pH range and high concentrations of electrolytes and/or other common detergent active ingredients. For example, test compositions structured with the materials of this invention and containing high concentrations of surfactant and/or high concentrations of electrolytes and/or high concentrations of HCl and/or high oxidative stress and/or significant enzyme activity still showed remarkable stability compared to known externals structuring agents.

In particular, as will be apparent from the apending examples, the present inventors have demonstrated that compositions structured with the particulate cellulose material of this invention are remarkably stable in the presence of high levels of electrolytes of various chemical natures and at different pH values. Additive and/or synergistic viscosity build-up with other (internal structuring) agents, such as surfactants and electrolytes, has even been observed. These properties make the external structuring agent of the present invention highly versatile.

The present inventors found that the particulate cellulose material of this invention, in certain embodiments, exhibits less flow instability as compared to compositions based on MFC and/or bacterial cellulose. More in particular, as can be inferred from the appended examples, liquid detergent or personal care products comprising the particulate cellulose material of this invention as the external structuring agent, do not have the zero or near zero stress-shear rate profile (i.e., zero stress-shear rate slope when plotting shear rate versus stress) observed when bacterial cellulose is used as the external structuring agent.

The particulate cellulose material of this invention is typically produced by subjecting parenchymal cell wall material to a process wherein part of the pectin an hemicellulose is removed and the resulting material is subjected to shear so as to reduce the particle size to a certain extent. In the present invention, said parenchymal cell wall material can be derived from a variety of vegetable pulp materials, such as sugar beet pulp. In particular, materials may be utilized that, at present, are still mainly considered by-products in various industries, such as sugar refining industry. Turning such by-products into a new natural resource, is obviously considered an advantage at present times, with ever growing concerns about overuse and wasting of natural resources.

The production of the present particulate cellulose material from these by-products, as will be described herein in greater detail, involves processing under generally mild conditions. As a result, also from a purely economical perspective, the material of this invention is more attractive as an external structuring agent in liquid detergent and personal care product than bacterial cellulose (with or without the addition of citrus fibre).

The particulate cellulose material of this invention can be provided in relatively concentrated forms, which are relatively easy to (re-)disperse into the liquid detergent products and/or personal care products. In particular it is not necessary to apply intensive processing steps in order to disperse the material, contrary to some of the prior art structuring agents.

The present inventors also established that the particulate cellulose material produced in accordance with this invention, if desired, can be subjected to a bleaching step without significant impact on the structuring properties of the material, as can be inferred from the appending examples. This is a further advantage as bleaching is sometimes desired for reasons of visual acceptability of the structured product, especially in terms of colour.

Without wishing to be bound by any particular theory, it is assumed that, in the cellulose particles of the invention, the organization of the cellulose fibrils as it exists in the parenchymal cell walls is at least partly retained, even though part of the pectin and hemicellulose is removed therefrom.

Furthermore, the cellulose based nanofibrils are not completely unraveled, i.e. the material is not primarily based on completely unraveled nanofibrils, but instead can be considered to comprise, as the main constituent, parenchymal cell wall debris, having substantial parts of the pectin and hemicellulose removed. The inventors hypothesize that at least some hemicellulose and/or pectin is to be retained in the material to support the structural organization of the cellulose in the particles, e.g. by providing an additional network. Such hemicellulose networks would hold the cellulose fibers together, thereby providing structural integrity and strength to the cellulose particle.

The present invention provides the new particulate cellulose based material as well as its production and its use as a structuring agent in liquid detergent products. These and other aspects of the invention will become apparent on the basis of the following detailed description and the appended examples.

DETAILED DESCRIPTION OF THE INVENTION

Figure 1A:
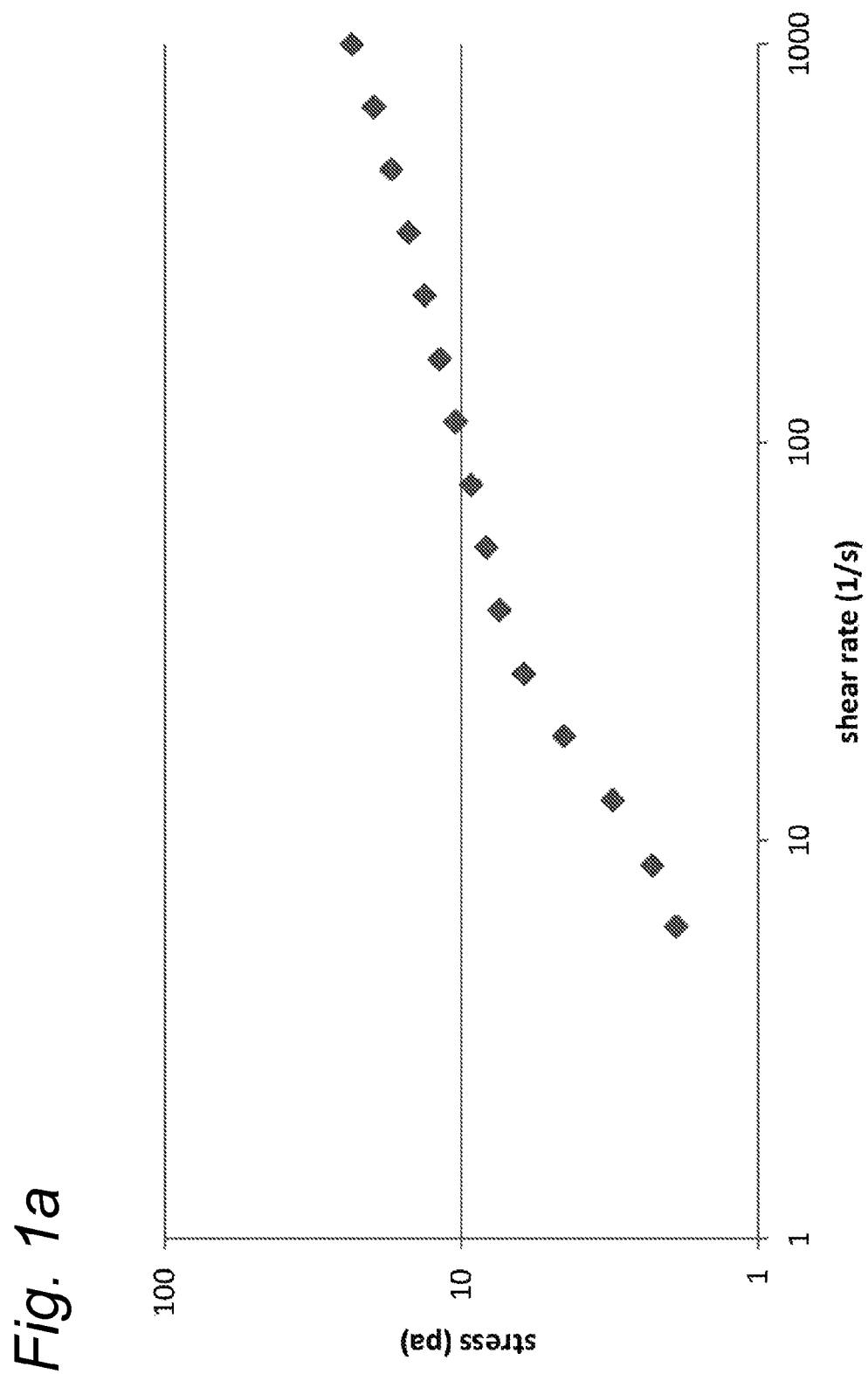
Figure 1a shows the stress vs. shear rate profile of a 0.5% (w/w) MCF in water system.

Hence, an aspect of the invention concerns a parenchymal cellulose composition comprising a particulate cellulose material containing, by dry weight of said particulate cellulose material, at least 70% cellulose, 0.5-10% pectin and at least 1-15% hemicellulose, wherein the particulate material has a volume-weighted median major particle dimension within the range of 25-75 µm, preferably within the range of 35-65 µm, as measured by laser light diffractometry.

Parenchymal cell walls contain relatively thin cell walls (compared to secondary cell walls) which are tied together by pectin. Secondary cell walls are much thicker than parenchymal cells and are linked together with lignin. This terminology is well understood in the art. Polysaccharides typically can make up 90% or more of the primary plant cell walls, cellulose, hemicelluloses and pectins being the main constituents. The precise morphology and (chemical) make-up of parenchymal cell walls may vary considerably from species to species. The parenchymal cellulose in accordance with the invention is preferably obtained from sugar beet, e.g. as a by-product of sucrose production.

The particulate cellulose material of this invention contains particles of specific structure, shape and size, as explained herein before. Typically the material contains particles having the form of platelets comprising parenchymal cellulose structures or networks. It is preferred that the size distribution of the particulate material falls within certain limits. When the distribution is measured with a laser light scattering particle size analyzer, such as the Malvern Mastersizer or another instrument of equal or better sensitivity, the diameter data is preferably reported as a volume distribution. Thus the reported median for a population of particles will be volume-weighted, with about one-half of the particles, on a volume basis, having diameters less than the median diameter for the population. Typically, the median major dimension of the particles of the parenchymal cellulose composition is within the range of 25-75 µm. More preferably the median major dimension of the particles of the parenchymal cellulose composition is within the range of 35-65 µm. Typically at least 90%, on a volume basis, of the particles has a diameter less than 120 µm, more preferably less than 110 µm, more preferably less than 100 µm. Preferably, the particulate cellulose material has a volume-weighted median minor dimension larger than 0.5 µm, preferably larger than 1 µm.

The term "cellulose" as used herein refers to homogeneous long chain polysaccharides comprised of β-D-glucose monomer units, of formula $(C_6H_{10}O_5)_n$, and derivatives thereof, usually found in plant cell walls in combination with lignin and any hemicellulose. The parenchymal cellulose of this invention may be obtained from a variety of plant sources containing parenchymal cell walls. Parenchymal cell wall, which may also be denoted as 'primary cell wall', refers to the soft or succulent tissue, which is the most abundant cell wall type in edible plants. Preferably the particulate cellulose material comprises, by dry weight, at least 70 wt %, preferably at least 80 wt %, more preferably at least 90 wt % of cellulose.

The compositions of this invention are characterized by the fact that the majority of the cellulose material is present in the form of particles that are distinct from the nanofibrilised cellulose described in the prior art in that the cellulose nanofibrils are not substantially unraveled, as discussed before. Preferably, less than 10%, or more preferably less than 1% or less than 0.1% by dry weight of the cellulose within the composition is in the form of nanofibrillated cellulose. This is advantageous as nanofibrillated cellulose negatively affects the redispersability of the material, as indicated herein before. By 'nanofibrils' we refer to the fibrils making up the cellulose fibers, typically having a width in the nanometer range and a length of between up to 20 µm. The nomenclature used in the field over the past decades has been somewhat inconsistent in that the terms 'microfibril' and 'nanofibril' have been used to denote the same material. In the context of this invention, the two terms are deemed to be fully interchangeable.

In accordance with the invention, the plant parenchymal cellulose material has been treated, modified and/or some components may have been removed but the cellulose at no time has been broken down to individual microfibrils, thereby losing the structure of plant cell wall sections.

As mentioned before, the cellulose material of this invention has a reduced pectin content, as compared to the parenchymal cell wall material from which it is derived. Removal of some of the pectin is believed to result in enhanced thermal stability. The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the L-rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction.

It is preferred that the particulate cellulose material of the invention comprises less than 5 wt. % of pectin, by dry weight of the particulate cellulose material, more preferably less than 2.5 wt. %. The presence of at least some pectin in the cellulose material is nevertheless desired. Without wishing to be bound by any theory it is assumed that pectin plays a role in the electrostatic interactions between particles contained in the material and/or in supporting the network/structure of the cellulose. Hence, it is preferred that the particulate cellulose material contains at least 0.5 wt % of pectin by dry weight of the particulate cellulose material, more preferably at least 1 wt %.

As mentioned before, the cellulose material of this invention has a certain minimum content of hemicellulose. The term "hemicellulose" refers to a class of plant cell-wall polysaccharides that can be any of several homo- or heteropolymers. Typical examples thereof include xylane, arabinane xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in molecular weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells. Without wishing to be bound by any theory, it is assumed that the presence of at least some hemicellulose is important to the structural organization of the fibers making up the particulate material. Preferably the particulate cellulose material comprises, by dry weight of the particulate cellulose material, 1-15 wt % hemicellulose, more preferably 1-10 wt % hemicellulose, most preferably 1-5 wt % hemicellulose.

The parenchymal cellulose composition of this invention typically can comprise other materials besides the particulate cellulose material, as will be understood by those skilled in the art. Such other materials can include, e.g., remnants from (the processing of) the raw plant cell wall source (other than the particulate cellulose material of the invention) and any sort of additive, excipient, carrier material, etc., added with a view to the form, appearance and/or intended application of the composition.

The compositions of this invention, typically may take the form of an aqueous suspension or paste like material comprising dispersed therein the particulate cellulose material of this invention. In an embodiment, an aqueous soft solid like dispersion is provided comprising at least 10% particulate cellulose material (on solid weight basis). The composition may comprise at least 20% particulate cellulose material (on solid weight basis). The composition may comprise at least 30% particulate cellulose material (on solid weight basis). In the context of this invention, these concentrated dispersions may also be referred to as structuring agents. These structuring agents may be added in certain quantities to surfactant systems in aqueous media to produce structured surfactant compositions.

A particulate cellulose material as described here above can be obtained using a specific process, which process involves a step of mild alkali treatment to hydrolyse the cell wall material followed by an intense homogenization process which does however not result in the complete unraveling of the material to its individual nanofibrils.

Accordingly, an aspect of the invention concerns a method of preparing a parenchymal cellulose composition as described in the foregoing, said method comprising the steps of;
a) providing a parenchyma cell containing vegetable pulp;
b) subjecting the parenchyma cell containing vegetable pulp to chemical and/or enzymatic treatment resulting in partial degradation and/or extraction of pectin and hemicellulose, wherein the mixture may be homogenized once or several times by applying low shear force during and/or after said chemical and/or enzymatic treatment;
c) subjecting the material resulting from step b) to a high shear process, wherein the particle size of the cellulose material is reduced so as to yield a particulate material having a volume-weighted median major dimension within the range of 25-75 µm, as measured by laser diffractiometry;
d) removing liquid from the mass obtained in step c).

The parenchyma cell containing vegetable pulp used as the starting material typically comprises an aqueous slurry comprising ground and/or cut plant materials, which often can be derived from waste streams of other processes, in particular sugar beet pulp.

Particularly preferred is the use of fresh, pressed-out sugar beet pulp from which the sugars have been extracted and which has a dry solids content of 10-50 wt. %, preferably 20-30 wt. %, for example approximately 25 wt. %. Sugar beet pulp is the production residuum from the sugar beet industry. More specifically, sugar beet pulp is the residue from the sugar beet after the extraction of sucrose there from. Sugar beet processors usually dry the pulp. The dry sugar beet pulp can be referred to as "sugar beet shreds". Additionally, the dry sugar beet pulp or shreds can be formed and compressed to produce "sugar beet pellets". These materials may all be used as the starting material, in which case step a) will comprise suspending the dry sugar beet pulp material in an aqueous liquid, typically to the afore-mentioned dry solids contents. Preferably however, fresh wet sugar beet pulp is used as the staring material.

Another preferred starting material is ensilaged sugar beet pulp. As used herein, the term "ensilage" refers to the conservation in a moist state of vegetable materials as a result of acidification caused by anaerobic fermentation of carbohydrates present in the materials being treated. Ensilage is carried out according to known methods with pulps preferably containing 15 to 35% of dry matter. Ensilage of sugar beets is continued until the pH is at least less than 5 and greater than 3.5. (see U.S. Pat. No. 6,074,856). It is known that pressed beet pulps may be ensilaged to protect them from unwanted decomposition. This process is most commonly used to protect this perishable product, the other alternative being drying to 90% dry matter. This drying has the disadvantage of being very energy-intensive. The fermentation process starts spontaneously under anaerobic conditions with the lactic acid bacteria present. These microorganisms convert the residual sucrose of the pressed beet pulp to lactic acid, causing a fall in the pH and hence maintaining the structure of the beet pulp.

In an embodiment of the invention the parenchyma cell containing vegetable pulp is washed in a flotation washer before the chemical or enzymatic treatment is carried out, in order to remove sand and clay particles and, in case ensilaged sugar beet pulp is used as a starting material, in order to remove soluble acids.

In accordance with the invention, the chemical and/or enzymatic treatment results in the degradation and/or extraction of at least a part of the pectin and hemicelluloses present in the parenchyma cell containing vegetable pulp, typically to monosaccharides, disaccharides and/or oligosaccharides. However, as indicated above, the presence of at least some non-degraded pectin, such as at least 0.5 wt %, and some non-degraded hemicellulose, such as 1-15 wt %, is preferred. Hence, step b) typically comprises partial degradation and/or extraction of the pectin and hemicellulose, preferably to the extent that at least 0.5 wt. % of pectin and at least 1 wt. % of hemicellulose remain. It is within the routine capabilities of those skilled in the art to determine the proper combinations of reaction conditions and time to accomplish this.

The term monosaccharide as used herein has its normal scientific meaning and refers to a monomeric carbohydrate unit. The term disaccharide as used herein has its normal scientific meaning and refers to a carbohydrate of two covalently bound monosaccharides. The term oligosaccharide as used herein has its normal scientific meaning and refers to a carbohydrate of three to ten covalently bound monosaccharides.

Preferably, the chemical treatment as mentioned in step b) of the above mentioned method comprises:
i) mixing the parenchyma cell containing vegetable pulp with a 0.1-1.0 M alkaline metal hydroxide, preferably 0.3-0.7 M alkaline metal hydroxide; and
ii) heating the mixture of parenchyma cell containing vegetable pulp and alkaline metal hydroxide to a temperature within the range of 80-120° C. for a period of at least 10 minutes, preferably at least 20 minutes, more preferably at least 30 minutes.

It has been found that the use of alkaline metal hydroxides, especially sodium hydroxide, in the above method, is necessary to remove pectin and hemicelluloses from the cellulose to the desired extent. The alkaline metal hydroxide may be sodium hydroxide. The alkaline metal hydroxide may be potassium hydroxide. The alkaline metal hydroxide may be at a concentration of at least 0.2 M, at least 0.3 M, or at least 0.4 M. The alkaline metal hydroxide, preferably is at less than 0.9 M, less than 0.8 M, less than 0.7 M or less than 0.6 M.

The use of relatively low temperatures in the present chemical process allows the vegetable material pulp to be processed with the use of less energy and therefore at a lower cost than methods known in the art employing higher temperatures. In addition, use of low temperatures and pressures ensures that minimum cellulose nanofibers are produced. Cellulose nanofibers affect the viscosity of the composition and make it more difficult to rehydrate the composition after dehydration. The vegetable material pulp may be heated to at least 80° C. Preferably, the vegetable material pulp is heated to at least 90° C. Preferably, the vegetable material pulp is heated to less than 120° C., preferably less than 100° C. As will be appreciated by those skilled in the art, the use of higher temperatures, within the indicated ranges, will reduce the processing times and vice versa. It is a matter of routine optimization to find the proper set of conditions in a given situation. As mentioned above, the heating temperature is typically in the range of 80-120° C. for at least 10 minutes, preferably at least 20 minutes, more preferably at least 30 minutes. If the heating temperature in step ii) is between 80-100° C., the heating time may be at least 120 minutes. Preferably, step ii) comprises heating the mixture to a temperature of 90-100° C. for 120-240 minutes, for example to a temperature of approximately 95° C. for 180 minutes. In another embodiment of the invention, the mixture is heated above 100° C., in which case the heating time can be considerably shorter. In a preferred embodiment of the present invention step ii) comprises heating the mixture to a temperature of 110-120° C. for 10-50 minutes, preferably 10-30 minutes.

Preferably or additionally, at least a part of the pectin and hemicelluloses may be degraded by treatment of the vegetable pulp with suitable enzymes. Preferably, a combination of enzymes is used, although it may also be possible to enrich the enzyme preparation with one or more specific enzymes to get an optimum result. Generally an enzyme combination is used with a low cellulase activity relative to the pectinolytic and hemicellulolytic activity. In a preferred embodiment of the present invention such a combination of enzymes, has the following activities, expressed as percentage of the total activity of the combination:

cellulase activity of 0-10%;
pectinolytic activity of 50-80%; and
hemicellulase activity of at least 20-40%

The enzyme treatments are generally carried out under mild conditions, e.g. at pH 3.5-5 and at 35-50° C., typically for 16-48 hours, using an enzyme activity of e.g. 65.000-150.000 units/kg substrate (dry matter). It is within the routine capabilities of those skilled in the art to determine the proper combinations of parameters to accomplish the desired rate and extent of pectin and hemicellulose degradation.

Before, during or after step b) the mixture is preferably homogenized once or several times by applying low shear force. Low shear force can be applied using standard methods and equipment known to those skilled in the art, such as conventional mixers or blenders. Preferably, the step of homogenisation at low shear is carried out for at least 5 minutes, preferably at least 10 minutes, preferably at least 20 minutes. Typically low shear mixing is done at least once during step b), preferably at least twice, more preferably at least three times. In a preferred embodiment of the invention low shear mixing is performed, for at least one fourth of the total duration of step b), preferably at least one third of the total time of step b), more preferably at least half the time. It has been found that it is advantageous to homogenise at low shear at this stage, as it helps breaking the pulp down into individual cells, which are then in turn, during the treatment of step c), broken up into cellulose platelets.

Step c) typically involves high shear treatment of the mass resulting from step b), which will typically result in cellulose platelets being e.g. less than half the size of the parent cells, preferably less than one third the size of the parent cells. As mentioned before, the inventors have found that it is important to retain part of the structure in the cellulose particles to ensure that the composition provides the advantageous characteristics described herein. As will be understood from the foregoing, the processing during step d) should not result in the complete or substantial unraveling to nanofibrils.

The process of obtaining the desired particle size characteristics of the cellulose material in step c) is not particularly limited and many suitable methods are known to those skilled in the art. Examples of suitable size reducing techniques include grinding, crushing or microfluidization. Suitably the process is conducted as wet processes, typically by subjecting the aqueous liquid from step b), which may e.g. contain 1 to 50% cellulosic material, to grinding, crushing, microfluidization or the like. Preferred grinding methods include: grinding using stirring blades such as unidirectional rotary-, multi-axis rotary-, reciprocal inverse-, vertical motion-, rotary and vertical motion-, and duct line-system stirring blades, such as portable mixers, solid mixers, and lateral mixers; jet-system stirring grinding using e.g. line mixers; grinding using high-shear homogenizers, high-pressure homogenizers, ultrasonic homogenizers, and the like; rotary extrusion-system grinding using kneaders; and grinding combining consolidation with shearing, such as roll mills, ball mills, vibratory ball mills, and bead mills. A suitable crushing method includes screen system crushing using e.g. screen mills and hammer mills; blade rotating shear screen system crushing using e.g. flash mills; air jet system crushing using e.g. jet mills; crushing combining consolidation with shearing, using e.g. roll mills, ball mills, vibratory ball mills, and bead mills; and a stirring blade system crushing method. These methods may be used alone or in combination. Most preferred examples of high shear equipment for use in step c) include friction grinders, such as the Masuko supermasscolloider; high pressure homogenizers, such as a Gaulin homogeninizer, high shear mixers, such as the Silverson type FX; in line homogenizer, such as the Silverson or Supraton in line homogenizer; and microfluidizers. The use of this equipment in order to obtain the particle properties required by this invention is a matter of routine for those skilled in the art. The methods described here above may be used alone or in combination to accomplish the desired size reduction.

In a preferred embodiment of the invention, heating is discontinued after step c) and the mass may be allowed to cool in between steps c) and d) or it may be transferred to the homogenizer directly, where no additional heating takes place. In a preferred embodiment step c) is performed at ambient temperature.

Preferably, the particle size of the cellulose is reduced before and a separation on the basis of particle size is subsequently carried out. Examples of useful separation techniques are sieve classification and separations using a cyclone or centrifuge.

The aim of the removal of water during step d) is primarily to remove a substantial fraction of dissolved organic material as well as a fraction of unwanted dispersed organic matter, i.e. having a particle size well below the particle size range of the particulate cellulose material.

In view of the first objective, it is preferred not to use methods relying on evaporation, as will be understood, since this will not remove any of the dissolved salts, pectin, proteins, etc., which are exactly the components to be washed out by this step. Preferably, step d) does not comprise a drying step, such as evaporation, vacuum drying, freeze-drying, spray-drying, etc. In one preferred embodiment of the invention, the mass may be subjected to microfiltration, dialysis, centrifuge decantation or pressing.

As will be understood by those skilled in the art, it is possible to incorporate multiple processing steps in order to achieve optimal results. For example, an embodiment is envisaged wherein step d) comprises subjecting the mixture to microfiltration, dialysis or centrifuge decantation, or the like, followed by a step of pressing the composition.

As will be understood by those skilled in the art, step d) may also comprise the subsequent addition of water or liquid followed by an additional step of removal of liquid, e.g. using the above described methods, to result in an additional washing cycle. This step may be repeated as many times as desired in order to achieve a higher degree of purity.

Preferably, following step d), the composition is added to an aqueous medium and the cellulose particles within the composition are rehydrated and uniformly suspended within the aqueous medium under low shear mixing. Rehydration under low shear mixing ensures that the energy cost to rehydrate is low and that the cellulose platelets are not damaged, or that a significant proportion of the cellulose platelets are not damaged during the mixing process.

Once compositions comprising the particulate cellulose material have been produced, it is often desirable to increase the concentration of the cellulose material to reduce the volume of the composition and thereby e.g. reduce storage and transport costs. Accordingly, the method produces a composition of cellulose platelets that is concentrated to at least 5 wt %, preferably at least 10 wt %, solids that may be then be added in small quantities to aqueous media comprising surfactant systems to provide distinctive structure. As mentioned before, the composition can be re-dispersed into aqueous media with low shear mixing. For example, the composition may be rehydrated and re-dispersed into aqueous media using a stirrer with paddles rotating with a tip speed of 1.3 m/s.

An aspect of the invention concerns the particulate cellulose material obtainable by any of the methods described herein.

Whenever, in this document, reference is made to 'the particulate cellulose material of the invention' this refers to the product as described herein on the basis of structural/chemical characteristics as well as to the products obtainable by the process described herein, which may be the same or different products.

A further aspect of the present invention concerns liquid detergent products and liquid personal care products comprising the particulate parenchymal cellulose material of the invention as an external structuring agent. The invention is not particularly limited with regard to the type of detergent products; the particulate parenchymal cellulose material of the invention can advantageously applied in laundry detergent products, hand and machine dishwashing detergents, liquid hard surface cleaning agents, industrial detergents and cleaning products, and personal hygiene products. As will be understood by those skilled in the art, the exact composition will depend on the type of product and the specific properties desired.

Hence, the invention generally provides liquid detergent products and liquid personal care products comprising (a) aqueous medium; (b) a surfactant system; and (c) external structuring agent; wherein said external structuring agent is or comprises the particulate cellulose material as described in any of the foregoing. In a particularly preferred embodiment of the invention such a liquid detergent product or liquid personal care product is provided comprising: (a) an aqueous medium; (b) 0.1-70% (w/w) of a surfactant system; and (c) 0.05-2.5% (w/w) of external structuring agent. In an even more preferred embodiment of the invention, such a liquid detergent product or liquid personal care product is provided comprising or consisting of: (a) an aqueous medium; (b) 0.1-70% (w/w) of a surfactant system; (c) 0.01-5 (w/w) % of an external structuring agent; and (d) 0-25% (w/w) of adjunct ingredients.

As used herein, the term "external structuring agent" refers to any material that is added to the liquid surfactant composition with the primary purpose of providing rheological and structuring benefits. An external structuring agent will not in itself provide any significant cleaning benefits. As such, an external structuring agent is distinct from detergent ingredients that also alter or affect the matrix rheology but are added primarily to provide some other benefit, especially to provide significant cleaning benefits. Such detergent ingredients may be generically referred to herein as "internal structuring agents".

The external structuring agent in accordance with the present invention comprises or consists of the particulate cellulose material of this invention. As will be understood from the foregoing, the particulate cellulose material of this invention as such can be provide in various diluted or concentrated forms but typically always has a certain water content. As will be understood by those skilled in the art, relative and absolute amounts of the particulate cellulose material in the liquid products of this invention, as appearing herein, concern the dry matter weight of the particulate cellulose material, unless indicated otherwise.

The content of external structuring agent in the liquid products of the invention can vary within a wide range. Advantageously, the liquid product of the invention comprises at least 0.01% (w/w), more preferably at least 0.05% (w/w), more preferably at least 0.1% (w/w), or at least 0.2% (w/w), or at least 0.3% (w/w), or at least 0.4% (w/w), or at least 0.5% (w/w) of external structuring agent. Advantageously, the liquid product of the invention comprises up to 5% (w/w), more preferably up to 2.5% (w/w), more preferably up to 2% (w/w), most preferably up to 1.5% (w/w), up to 1.2% (w/w), up to 1.1% (w/w), up to 1.0% (w/w), up to 0.9% (w/w), up to 0.8% (w/w), up to 0.7% (w/w) or up to 0.6% (w/w) of external structuring agent.

In one embodiment, the external structuring system further comprises additional structuring agents such as non-polymeric crystalline hydroxyl-functional materials, polymeric structuring agents, and mixtures thereof. One suitable additional structuring agent comprises a non-polymeric, crystalline hydroxyl-functional material, which forms thread-like structuring systems throughout the liquid matrix when they are crystallized within the matrix in situ. Such materials can be generally characterized as crystalline, hydroxyl-containing fatty acids, fatty esters or fatty waxes. Other types of organic structuring agents, besides the non-polymeric, crystalline, hydroxyl-containing structuring agents described hereinbefore, may be utilized in the liquid products of this invention. Polymeric materials which will provide shear-thinning capabilities to the liquid matrix may also be employed. Suitable polymeric structuring agents include those of the polyacrylate, polysaccharide or polysaccharide derivative type. Polysaccharide derivatives typically used as structuring agents comprise polymeric gum materials. Such gums include pectine, alginate, arabinogalactan (gum Arabic), carrageenan, gellan gum, xanthan gum and guar gum.

It has importantly been found that the external structuring system of the present invention provides sufficient rheological benefits, such as bead suspension and shear thinning capabilities, without reliance on structuring ingredients beyond the particulate cellulose material of this invention. Hence, in one embodiment, the external structuring agent consists entirely of the particulate cellulose material of this invention. Advantageously, the liquid detergent product or liquid personal care product of the invention comprises at least 0.01% (w/w), more preferably at least 0.05% (w/w), more preferably at least 0.1% (w/w), or at least 0.2% (w/w), or at least 0.3% (w/w), or at least 0.4% (w/w), or at least 0.5% (w/w) of the particulate cellulose material of the invention. Advantageously, the liquid product of the invention comprises up to 5% (w/w), more preferably up to 2.5% (w/w), more preferably up to 2% (w/w), most preferably up to 1.5% (w/w), up to 1.2% (w/w), up to 1.1% (w/w), up to 1.0% (w/w), up to 0.9% (w/w), up to 0.8% (w/w), up to 0.7% (w/w) or up to 0.6% (w/w) of the particulate cellulose material of the invention.

In an embodiment of the invention, the liquid detergent product does not contain external structuring agents other than the particulate cellulose material of this invention.

Furthermore, in an embodiment of the invention, the liquid detergent product or liquid personal care product comprises less than 0.05% (w/w) of bacterial cellulose. In a preferred embodiment of the invention, the liquid detergent product or liquid personal care product comprises less than 0.025% (w/w) of bacterial cellulose, more preferably less than 0.01% (w/w). Most preferably, the liquid detergent product of the invention is substantially or entirely devoid of bacterial cellulose.

Furthermore, in an embodiment of the invention, the liquid detergent product or liquid personal care product comprises less than 0.001% (w/w) of citrus fibres. In a preferred embodiment of the invention, the liquid detergent product or liquid personal care product comprises less than 0.0005 (w/w) of citrus fibres, more preferably less than 0.00025% (w/w). Most preferably, the liquid detergent product of the invention is substantially or entirely devoid of citrus fibres.

Furthermore, in an embodiment of the invention, the liquid detergent product or liquid personal care product comprises less than 0.05% (w/w) of water soluble polymer or polymers having a molecular weight of 100-1,000,000. In a preferred embodiment of the invention, the liquid detergent product or liquid personal care product comprises less than 0.025% (w/w) of such water-soluble polymers, more preferably less than 0.01% (w/w). Most preferably, the liquid detergent product of the invention is substantially or entirely devoid of such water-soluble polymers.

In accordance with this invention, the Surfactant system can be a surfactant or combination of surfactants, typically selected from the group consisting of anionic surfactants, cationic surfactants, nonionic surfactants, amphoteric surfactants and zwitterionic surfactants. The surfactant system is selected based on the desired application. Suitable surfactants include any conventional surfactants known for use in detergent products. Surfactants that provide some structuring and rheology modifying benefits constitute internal structuring agents and, as such, are distinct from external structuring agents and not encompassed by the term external structuring agent.

The content of the surfactant system in the liquid detergent product or liquid personal care product can vary within a wide range. Advantageously, the liquid detergent product or liquid personal care product of the invention comprises at least 0.1% (w/w), more preferably at least 0.5% (w/w), more preferably at least 1% (w/w), most preferably at least 2.5% (w/w), at least 5% (w/w) or at least 10% (w/w) of surfactant system. Advantageously, the liquid detergent product or liquid personal care product of the invention comprises up to 70% (w/w), more preferably up to 50% (w/w), more preferably up to 40% (w/w), most preferably up to 35% (w/w), up to 30% (w/w), up to 25% (w/w), up to 20% (w/w) or up to 15% (w/w) of surfactant system.

In one embodiment, the liquid detergent product or liquid personal care product comprises a weight ratio of surfactant system to external structurant within the range of from 1:1 to 5000:1, preferably from 100:1 to 2000:1, preferably from 500:1 to 1000:1. Importantly, although the amounts of both external structurant and surfactants can vary, the present invention is capable of providing suitable shear thinning capabilities and yield stress with higher amounts of external structurant to surfactant system, such as greater than 1000:1.

Suitable anionic surfactants include the alkyl sulfonic acids, alkyl benzene sulfonic acids, ethoxylated alkyl sulfates and their salts as well as alkoxylated or un-alkoxylated alkyl sulfate materials. In one embodiment, the anionic surfactant comprises an alkali metal salt of $C_{10-16}$ alkyl benzene sulfonic acids, preferably $C_{11-14}$ alkyl benzene sulfonic acids. In one embodiment, the alkyl group is linear and such linear alkyl benzene sulfonates are known as "LAS". Alkyl benzene sulfonates, and particularly LAS, are well known in the art. Other suitable anionic surfactants include: sodium and potassium linear straight chain alkylbenzene sulfonates in which the average number of carbon atoms in the alkyl group is from 11 to 14. Sodium $C_{11}$-$C_{14}$ e.g., $C_{12}$, LAS is one suitable anionic surfactant for use herein. Another suitable anionic surfactant comprises ethoxylated alkyl sulfate surfactants. Such materials, also known as alkyl ether sulfates or alkyl polyethoxylate sulfates, are those which correspond to the formula: R'—O—$(C_2H_4O)_n$—$SO_3M$; wherein R' is a $C_8$-$C_{20}$ alkyl group, n is from 1 to 20, and M is a salt-forming cation; alternatively, R' is $C_{10}$-$C_{18}$ alkyl, n is from 1 to 15, and M is sodium, potassium, ammonium, alkylammonium, or alkanolammonium. In another embodiment, R' is a $C_{12}$-$C_{16}$, n is from 1 to 6 and M is sodium. The alkyl ether sulfates will generally be used in the form of mixtures comprising varying R' chain lengths and varying degrees of ethoxylation. Frequently such mixtures will inevitably also contain some unethoxylated alkyl sulfate materials, i.e., surfactants of the above ethoxylated alkyl sulfate formula wherein n=0. Unethoxylated alkyl sulfates may also be added separately to the compositions of this invention and used as or in any anionic surfactant component which may be present. Suitable unalkoyxylated, e.g., unethoxylated, alkyl ether sulfate surfactants are those produced by the sulfation of higher $C_8$-$C_{20}$ fatty alcohols. Conventional primary alkyl sulfate surfactants have the general formula of: $ROSO_3M^+$, wherein R is typically a linear $C_8$-$C_{20}$ hydrocarbyl group, which may be straight chain or branched chain, and M is a water-solubilizing cation; alternatively R is a $C_{10}$-$C_{15}$ alkyl, and M is alkali metal. In one embodiment, R is $C_{12}$-$C_{14}$ and M is sodium. One embodiment provides a liquid detergent or personal care product comprising from 10% (w/w) to 35% (w/w) of an anionic surfactant comprising: $C_{10-16}$ linear alkylbenzene sulfonates, $C_{8-20}$ alkyl polyethoxylate sulfates having from 1 to 20 moles of ethylene oxide, $C_{8-16}$ alcohol polyethoxylates having from 1 to 16 moles of ethylene oxide, and mixtures thereof.

Where the liquid product of the invention is for personal care (i.e. shampoo or body wash), the anionic surfactant typically can include: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosimnate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and mixtures thereof.

Suitable nonionic surfactants include any of the conventional nonionic surfactant types typically used in liquid cleaning compositions. These include alkoxylated fatty alcohols, ethylene oxide (EO)-propylene oxide (PO) block polymers, and amine oxide surfactants. Suitable for use in the liquid cleaning compositions herein are those nonionic surfactants which are normally liquid. Suitable nonionic surfactants for use herein include the alcohol alkoxylate nonionic surfactants. Alcohol alkoxylates are materials which correspond to the general formula of: $R^1(C_mH_{2m}O)_nOH$, wherein $R^1$ is a $C_8$-$C_{16}$ alkyl group, m is from 2 to 4, and n ranges from 2 to 12; alternatively $R^1$ is an alkyl group, which may be primary or secondary, that contains from 9 to 15 carbon atoms, preferably from 10 to 14 carbon atoms. In another embodiment, the alkoxylated fatty alcohols will be ethoxylated materials that contain from 2 to 12, preferably 3 to 10, EO moieties per molecule. The alkoxylated fatty alcohol materials useful in the liquid compositions herein will frequently have a hydrophilic-lipophilic balance (HLB) which ranges from 3 to 17, preferably from 6 to 15, preferably from 8 to 15. Alkoxylated fatty alcohol nonionic surfactants have been marketed under the tradenames Neodol and Dobanol by the Shell Chemical Company. Another nonionic surfactant suitable for use includes ethylene oxide (EO)-propylene oxide (PO) block polymers, such as those marketed under the tradename Pluronic. These materials are formed by adding blocks of ethylene oxide moieties to the ends of polypropylene glycol chains to adjust the surface active properties of the resulting block polymers. Yet another suitable type of nonionic surfactant useful herein comprises the amine oxide surfactants. In one embodiment of the present invention, liquid product comprises 0.1-20% (w/w), preferably 1-15% (w/w), preferably 3.0-10% (w/w) of an amine oxide surfactant. Amine oxides are often referred to in the art as "semi-polar" nonionics, and have the formula: $R(EO)_x(PO)_y(BO)_zN(O)(CH_2R')_2.qH_2O$. In this formula, R is a relatively long-chain hydrocarbyl moiety which can be saturated or unsaturated, linear or branched, and can typically contain from 8 to 20, preferably from 10 to 16 carbon atoms, and preferably a $C_{12}$-$C_{16}$ primary alkyl. R' is a short-chain moiety such as a hydrogen, methyl and —$CH_2OH$. When x+y+z is different from 0, EO is ethyleneoxy, PO is propyleneneoxy and BO is butyleneoxy, i.e. $C_{2-14}$ alkyldimethyl amine oxide.

In one embodiment, the surfactant system comprises anionic and nonionic surfactant at a weight ratio of from 100:1 to 1:100, preferably from 20:1 to 1:20, preferably from 2.5:1 to 18:1.

Suitable cationic surfactants are quaternary ammonium surfactants. Suitable quaternary ammonium surfactants are selected from the group consisting of mono $C_6$-$C_{16}$, preferably $C_6$-$C_{10}$ N-alkyl or alkenyl ammonium surfactants, wherein the remaining N positions are substituted by methyl, hydroxyehthyl or hydroxypropyl groups. Another preferred cationic surfactant is an $C_6$-$C_{18}$ alkyl or alkenyl ester of an quaternary ammonium alcohol, such as quaternary chlorine esters. More preferably, the cationic surfactants have the formula $X^-[(N^+R^1CH_3CH_3)-(CH_2CH_2O)_nH]$, wherein R1 is $C_8$-$C_{18}$ hydrocarbyl and mixtures thereof, preferably $C_{8-14}$ alkyl, preferably $C_8$, $C_{10}$ or $C_{12}$ alkyl, and X is an anion such as chloride or bromide.

Other suitable surfactants include amphoteric surfactants, zwitterionic surfactants, and mixtures thereof. Suitable amphoteric surfactants for uses herein include amido propyl betaines and derivatives of aliphatic or heterocyclic secondary and ternary amines in which the aliphatic moiety can be straight chain or branched and wherein one of the aliphatic substituents contains from 8 to 24 carbon atoms and at least one aliphatic substituent contains an anionic water-solubilizing group. When present, amphoteric surfactants typically comprise from 0.01% to 20%, preferably from 0.5% to 10% by weight of the liquid product of the invention.

Where the liquid product of the invention is a detersive composition, it can typically contain 0-15% (w/w), preferably 0.1-15% (w/w), preferably 0.2-10% (w/w), preferably 0.25-6% (w/w), preferably 0.5-1.5% (w/w) of at least one diamine. Suitable organic diamines are those in which pK1 and pK2 are in the range of 8.0 to 11.5, preferably in the range of 8.4 to 11, preferably from 8.6 to 10.75. Suitable materials include 1,3-bis(methylamine)-cyclohexane (pKa=10 to 10.5), 1,3 propane diamine (pK1=10.5; pK2=8.8), 1,6 hexane diamine (pK1=11; pK2=10), 1,3 pentane diamine (DYTEK EP™) (pK1=10.5; pK2=8.9), 2-methyl 1,5 pentane diamine (DYTEK A™) (pK1=11.2; pK2=10.0). Other suitable diamines include primary/primary diamines with alkylene spacers ranging from $C_4$ to $C_8$.

In one embodiment of the present invention, said surfactant system is free or essentially free of any of said above surfactants, for example: free or essentially free of non-ionic surfactant, free or essentially free of cationic surfactant.

As used herein, the term "Adjunct ingredients" refers to further ingredients that may typically be present in detergent products and/or personal care products to provide further benefits in terms of cleaning power, solubilization, appearance, fragrance, etc. The liquid detergent or personal care product can comprise a variety of adjunct ingredients. In one embodiment, the liquid detergent or personal care product preferably comprises at least 0.01% (w/w), at least 0.025% (w/w), at least 0.05% (w/w), at least 0.1% (w/w), at least 0.25% (w/w), at least 0.5% (w/w), at least 1% (w/w), at least 2% (w/w), at least 3% (w/w), at least 4% (w/w) or at least 5% (w/w) of adjunct ingredients. In one embodiment, the liquid detergent or personal care product preferably comprises up to 25% (w/w), up to 20% (w/w), up to 15% (w/w), up to 12.5% (w/w), up to 10% (w/w), up to 9% (w/w), up to 8% (w/w), up to 7% (w/w), up to 6% (w/w), or up to 5% (w/w) of adjunct ingredients.

In accordance with this invention, the liquid products of this invention may include Inorganic and/or organic builder. The term "Builder" is used herein to refer to additives which are useful primarily as a means of preventing or ameliorating the adverse effects on washing of calcium and magnesium ions e.g. by chelation, sequestering, precipitation or absorption of the ions, and secondarily as a source of alkalinity and buffering, in the latter sense. Inorganic builders include, for example, alkali metal, ammonium and alkanolammonium salts of polyphosphates, such as, for example, tripolyphosphates, pyrophosphates and glasslike polymeric metaphosphates, phosphonates, silicates, carbonates including bicarbonates and sesquicarbonates, sulfates and alumosilicates. Examples of silicate builders are the alkali metal silicates, in particular those with an $SiO_2:Na_2O$ ratio between 1.6:1 and 3.2:1, and phyllosilicates. For example sodium phyllosilicates obtainable from Clariant GmbH under the tradename SKS™. SKS-6™ is a particularly preferred phyllosilicate builder. Alumosilicate builders are, in particular, zeolites with the formula $Na_z[(AlO_2)_z(SiO_2)_y]_xH_2O$, in which z and y are integers of at least 6, the ratio of z to y is from 1.0 to 0.5, and x is an integer from 15 to 264. Suitable ion exchangers based on alumosilicate are available commercially. Other suitable builders include the ether hydroxypolycarboxylates, copolymers of maleic anhydride with ethylene or vinyl methyl ether, 1,3,5-trihydroxybenzene-2,4,6-trisulfonic acid and carboxymethyloxysuccinic acid, the alkali metal, ammonium and substituted ammonium salts of polyacetic acids, such as, for example, ethylenediaminetetraacetic acid and nitrilotriacetic acid, and polycarboxylic acids, such as mellitic acid, succinic acid, oxydisuccinic acid, polymaleic acid, benzene-1,3,5-tricarboxylic acid, carboxymethyloxysuccinic acid, and the soluble salts thereof. Organic builders are also polycarboxylates based on acrylic acid and maleic acid, such as, for example, the Sokalan CP grades from BASF. Builders based on citrate, e.g. citric acid and its soluble salts, in particular the sodium salt, are preferred polycarboxylic acid builders, which can also be used in granulated formulations, in particular together with zeolites and/or phyllosilicates. When employed, a builder may typically be present at a level of up to 15% (w/w), preferably from 0.05 to 10% (w/w), preferably from 0.1 to 5% (w/w) in the liquid detergent or personal care product.

In accordance with this invention, the liquid products of this invention may include electrolytes as adjunct ingredient. The term "electrolyte" is used herein to denote those water soluble ionic compounds which dissociate at least partially in aqueous solution to provide ions, and which tend to lower the solubility or micellar concentration of surfactants in such solutions by a "salting out" effect. It includes water soluble dissociable, inorganic salts such as, for example alkali metal or ammonium sulphates, chlorides, nitrates, phosphates, carbonates, silicates, perborates and polyphosphates, and also certain water soluble organic salts which desolubilise or "salt out" surfactants. Suitable inorganic salts include $MgI_2$, $MgBr_2$, $MgCl_2$, $Mg(NO_3)_2$, $Mg_3(PO_4)_2$, $Mg_2P_2O_7$, $MgSO_4$, magnesium silicate, NaI, NaBr, NaCl, NaF, $Na_3(PO_4)$, $NaSO_3$, $Na_2SO_4$, $Na_2SO_3$, $NaNO_3$, $NaIO_3$, $Na_3(PO_4)$, $Na_4P_2O_7$, sodium silicate, sodium metasilicate, sodium tetrachloroaluminate, sodium tripolyphosphate (STPP), $Na_2Si_3O_7$, sodium zirconate, $CaF_2$, $CaCl_2$, $CaBr_2$, $CaI_2$, $CaSO_4$, $Ca(NO_3)_2$, Ca, KI, KBr, KCl, KF, $KNO_3$, $KIO_3$, $K_2SO_4$, $K_2SO_3$, $K_3(PO_4)$, $K_4(P_2O_7)$, potassium pyrosulfate, potassium pyrosulfite, LiI, LiBr, LiCl, LiF, $LiNO_3$, $AlF_3$, $AlCl_3$, $AlBr_3$, $AlI_3$, $Al_2(SO_4)_3$, $Al(PO_4)$, $Al(NO_3)_3$, aluminum silicate; including hydrates of these salts and including combinations of these salts or salts with mixed cations e.g. potassium alum $AlK(SO_4)_2$ and salts with mixed anions, e.g. potassium tetrachloroaluminate and sodium tetrafluoroaluminate. Salts incorporating cations from groups IIIa, IVa, Va, VIa, VIIa, VIII, Ib, and IIb on the periodic chart with atomic numbers >13 are also useful but less preferred due to their tendency to change oxidation states and thus they can adversely affect the odor or color of the formulation or lower weight efficiency. Salts with cations from group Ia or Ia with atomic numbers >20 as well as salts with cations from the lactinide or actinide series are useful but less preferred due to lower weight efficiency or toxicity. Mixtures of above salts are also useful. Organic salts useful in this invention include, magnesium, sodium, lithium, potassium, zinc, and aluminum salts of the carboxylic acids including formate, acetate, proprionate, pelargonate, citrate, gluconate, lactate aromatic acids e.g. benzoates, phenolate and substituted benzoates or phenolates, such as phenolate, salicylate, polyaromatic acids terephthalates, and polyacids e.g. oxylate, adipate, succinate, benzenedicarboxylate, benzenetricarboxylate. Other useful organic salts include carbonate and/or hydrogencarbonate ($HCO_3^{-1}$) when the pH is suitable, alkyl and aromatic sulfates and sulfonates e.g. sodium methyl sulfate, benzene sulfonates and derivatives such as xylene sulfonate, and amino acids when the pH is suitable. Electrolytes can comprise mixed salts of the above, salts neutralized with mixed cations such as potassium/sodium tartrate, partially neutralized salts such as sodium hydrogen tartrate or potassium hydrogen phthalate, and salts comprising one cation with mixed anions. Generally, inorganic electrolytes are preferred over organic electrolytes for better weight efficiency and lower costs. Mixtures of inorganic and organic salts can be used. Typical levels of electrolyte in the compositions, if employed, are up to 10% (w/w), preferably from 0.5 to 5% (w/w), more preferably from 0.75 to 2.5% (w/w), and most preferably from 1 to 2% (w/w).

In one embodiment, the liquid detergent or personal care product comprises suspension particles at a level of from 0.01 to 5% (w/w), preferably from 0.05 to 4% (w/w), preferably from 0.1 to 3% (w/w). In one embodiment, the suspension particles have a particle size in the range from 100 nm to 8 mm. As defined herein, "particle size" means that at least one of said suspension particles have a longest linear dimension as defined. Those of skill in the art will understand that suitable techniques to measure particle size are available. It has importantly been found that the liquid products of the present invention are capable of suspending a vast range of particles, from visibly distinct particles with particle size up to 8 mm to pearlescence agents which have particle sizes typically below 500 μm. In one embodiment, the particle size is from 0.1 mm to 8 mm, preferably from 0.3 mm to 3 mm, and preferably from 0.5 to 4 mm. In another embodiment, the suspension particles are not visibly distinct and have a particle size of from 1 nm to 500 μm, preferably from 1 μm to 300 μm, preferably from 50 μm to 200 μm. The suspension particles useful herein typically have a density of from 700 $kg/m^3$ to 4,260 $kg/m^3$, preferably from 800 $kg/m^3$ to 1,200 $kg/m^3$, preferably from 900 $kg/m^3$ to 1,100 $kg/m^3$, preferably from 940 $kg/m^3$ to 1,050 $kg/m^3$, preferably from 970 kg/m³ to 1,047 kg/m³, preferably from and 990 kg/m³ to 1,040 kg/m³ at 25° C. The liquid detergent or personal care product of the present invention is typically capable of suspending particles for 4 weeks at 25° C. A freshly made composition of the present invention is considered to be stable if less than 10%, preferably less than 5% and more preferably less than 1% by weight of the particles settle to the bottom of the container after 4 weeks of static storage. In one embodiment, the difference between the density of the liquid matrix and the density of the particles is less than 10% of the liquid matrix density, preferably less than 5%, preferably less than 3%, preferably less than 1%, preferably less than 0.5%, at 25° C. In another embodiment, the liquid matrix and the suspension particle have a density difference of from 1 kg/m³ to 3,260 kg/m³, preferably from 10 kg/m³ to 200 kg/m³, preferably from 50 kg/m³ to 100 kg/m³. In an embodiment the liquid detergent or personal care product comprises from 0.1 to 2% (w/w) of suspension particles in the range of 50 to 750 microns of particle size, such as a Silica-$TiO_2$ particles which function as sensory and skin exfoliating signals and a grease removal enhancing agent on dishes. Additionally, polyethylene beads and butylene/ethylene copolymers of a particle size ranging from 50 to 350 microns can be used.

In one embodiment, the liquid detergent or personal care product may comprise a polycarboxylate polymer, a copolymer comprising one or more carboxylic acid monomers. A water soluble carboxylic acid polymer can be prepared by polymerizing a carboxylic acid monomer or copolymerizing two monomers, such as an unsaturated hydrophilic monomer and a hydrophilic oxyalkylated monomer. Examples of unsaturated hydrophilic monomers include acrylic acid, maleic acid, maleic anhydride, methacrylic acid, methacrylate esters and substituted methacrylate esters, vinyl acetate, vinyl alcohol, methylvinyl ether, crotonic acid, itaconic acid, vinyl acetic acid, and vinylsulphonate. The hydrophilic monomer may further be copolymerized with oxyalkylated monomers such as ethylene or propylene oxide. The hydrophilic oxyalkyated monomer preferably has a solubility of 500 grams/liter, more preferably 700 grams/liter in water. The unsaturated hydrophilic monomer may further be grafted with hydrophobic materials such as poly(alkene glycol) blocks.

The liquid product optionally comprises a hydrotrope so that the product is compatible in water. Suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof. If included, hydrotropes are typically present at a level of up to 15% (w/w), e.g. 1 to 10% (w/w), or 3 to 6% (w/w).

The liquid product of the present invention may optionally contain a polymeric suds stabilizer. These polymeric suds stabilizers provide extended suds volume and suds duration of the product. These polymeric suds stabilizers may be selected from homopolymers of (N,N-dialkylamino) alkyl esters and (N,N-dialkylamino)alkyl acrylate esters. The weight average molecular weight of the polymeric suds boosters, determined via conventional gel permeation chromatography, is from 1,000 to 2,000,000, preferably from 5,000 to 1,000,000, preferably from 10,000 to about 750,000, preferably from 20,000 to 500,000, preferably from 35,000 to 200,000. The polymeric suds stabilizer can optionally be present in the form of a salt, either an inorganic or organic salt, for example the citrate, sulfate, or nitrate salt of (N,N-dimethylamino)alkyl acrylate ester. One suitable polymeric suds stabilizer is (N,N-dimethylamino)alkyl acrylate esters. When present, the polymeric suds booster may typically be present at a level of up to 15% (w/w), preferably from 0.05 to 10% (w/w), preferably from 0.1 to 5% (w/w) in the liquid detergent or personal care product.

The liquid product according to the present invention may comprise a linear or cyclic carboxylic acid or salt thereof to improve the rinse feel. The presence of anionic surfactants, especially when present in higher amounts in the region of 15-35% (w/w), results in the liquid detergent and personal care product imparting a slippery feel to the hands, which can be reduced using the carboxylic acids as defined herein. Carboxylic acids useful herein include salicylic acid, maleic acid, acetyl salicylic acid, 3 methyl salicylic acid, 4 hydroxy isophthalic acid, dihydroxyfumaric acid, 1,2,4 benzene tricarboxylic acid, pentanoic acid and salts thereof and mixtures thereof. Where the carboxylic acid exists in the salt form, the cation of the salt is selected from alkali metal, alkaline earth metal, monoethanolamine, diethanolamine or triethanolamine and mixtures thereof. If included, the carboxylic acid or salt thereof is typically present at a level of up to 5% (w/w), e.g. from 0.2 to 1% (w/w), preferably from 0.25 to 0.5% (w/w).

Organic solvents may be employed in the liquid products of this invention. Suitable organic solvents include $C_{4-14}$ ethers and diethers, glycols, alkoxylated glycols, $C_{6-16}$ glycol ethers, alkoxylated aromatic alcohols, aromatic alcohols, aliphatic branched alcohols, alkoxylated aliphatic branched alcohols, alkoxylated linear $C_{1-5}$ alcohols, linear $C_{1-5}$ alcohols, amines, $C_{8-14}$ alkyl and cycloalkyl hydrocarbons and halohydrocarbons, and mixtures thereof. In one embodiment, the liquid detergent or personal care product comprises from 0.01 to 20% (w/w), preferably from 0.5 to 15% (w/w), preferably from 1 to 10% (w/w) by weight of said organic solvent.

The liquid product according to the present invention, typically when it is a detergent product, such as a laundry detergent, may comprise one or more detersive enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, mannanases, pentosanases, malanases, β-glucanases, arabinosidases, hyaluronidase, chondroitinase, laccase, and known amylases, and combinations thereof. A preferred enzyme combination comprises a cocktail of conventional detersive enzymes like protease, lipase, cutinase and/or cellulase in conjunction with amylase. If employed, enzyme is typically present at a level of up to 5% (w/w), e.g. from 0.0001 to 0.5% (w/w), preferably from 0.001 to 0.1% (w/w). Importantly, the present external structuring agent is believed to provide sufficient structuring capabilities, including bead suspension and shear thinning capabilities, in the presence of detersive enzymes for extended periods of time.

In an embodiment of the invention, the liquid detergent product comprises less than 0.0001 wt % of enzyme selected from lipase, cellulase and mixtures thereof. In a preferred embodiment of the invention, the liquid detergent product does not comprise lipase, cellulase and/or mixtures thereof.

The liquid product according to the present invention, typically when it is a detergent product, such as a laundry detergent, may comprise one or more bleaching agents. Among those compounds acting as bleaching agents which release $H_2O_2$ in water, sodium percarbonate, sodium perborate tetrahydrate and sodium perborate monohydrate are of particular significance. Further usable bleaching agents are, for example, peroxypyrophosphates, citrate perhydrates and $H_2O_2$-releasing per-acidic salts or per-acids, such as perbenzoates, peroxophthalates, diperazelaic acid, phthaloimino per-acid or diperdodecanedioic acid. Bleaching agents from the group of organic bleaching agents may furthermore also be used. Typical organic bleaching agents are diacyl peroxides, such as for example dibenzoyl peroxide. Further typical organic bleaching agents are peroxy acids, e.g. alkylperoxy acids and arylperoxy acids. If employed in the products of this invention, bleaching agent is typically present at levels of 1 to 20% (w/w), preferably 2 to 15% (w/w) and in particular 4 to 12% (w/w). Importantly, the present external structuring agent is believed to provide sufficient structuring capabilities, including bead suspension and shear thinning capabilities, in the presence of bleaching agent for extended periods of time.

Additional adjunct components include optical brighteners, typically at levels of from 0.01 to 1% (w/w); dye transfer inhibition agents, typically at levels of from 0.0001 to 10% (w/w); suds suppressors, typically at levels of from 0.001 to 2% (w/w); soil release polymers, typically at levels of from 0.01 to 10% (w/w); silicone polymers, typically at levels of from 0.01 to 25% (w/w); perfumes; dyes; opacifiers; chelants; and pH adjusting and/or buffering agents.

In one embodiment the liquid product of the invention is a liquid laundry detergent and one or more of the disclosed adjunct components are included in the formulation. Suitable adjunct components for a liquid laundry detergent include: detersive enzymes, optical brighteners, dye transfer inhibition agents, suds suppressors, detersive soil release polymers, other fabric care benefit agents, stabilizers, ancillary detersive surfactants, detersive builders, perfumes, coloring agents, enzymes, bleaches, mal-odor control agents, antimicrobials, anti-static agents, fabric softening agents, grease cleaning polymers including graft polymers, and combinations of thereof. All of these materials are of the type conventionally utilized in laundry detergent products. They can, however, be delivered to aqueous washing liquors, and/or to fabrics being laundered therein, especially effectively via the compositions of the present invention.

The term "Aqueous medium" is used herein to generally refer to the solvent, which contains water as the main constituent, although certain amounts of other solvents may be comprised in the medium, as will be appreciated by those skilled in the art. In an embodiment, the liquid product of the invention comprises water in an amount of at least 1% (w/w), more preferably at least 5% (w/w), more preferably at least 10% (w/w), more preferably at least 20% (w/w), more preferably at least 25% (w/w), more preferably at least 30% (w/w). Furthermore, In an embodiment, the liquid product of the invention comprises water in an amount of less than 85% (w/w), more preferably less than 75% (w/w), more preferably less than 70% (w/w), more preferably less than 60% (w/w), more preferably less than 50% (w/w), more preferably less than 40% (w/w), more preferably less than 35% (w/w). In one embodiment the liquid detergent or personal care product is a concentrated formulation comprising as low as 1 to 30% (w/w) water, preferably from 5 to 15% (w/w), preferably from 10 to 14% (w/w). Concentrated formulations would be particularly desirable for embodiments where the liquid product is encapsulated in a unit dose article.

In one embodiment, the liquid detergent or personal care product has a pH of from 6 to 14, preferably from 6 to 13, preferably from 6 to 10, alternatively an basic pH of greater than about 7. It has importantly been found that the particulate cellulose material is capable of providing the desired structuring benefits at pH values of above 7, or above 10.

In one embodiment, the liquid detergent or personal care product has a pH of below 6, preferably below 5, more preferably below 4, more preferably below 3, more preferably below 2, more preferably below 1. It has importantly been found that the particulate cellulose material is capable of providing the desired structuring benefits at extremely low pH values. Preferably, in accordance with this embodiment, the liquid product of the invention is a detergent product, in particular a product for cleaning hard surfaces and/or an industrial detergent product.

The ability of a liquid product of the invention to suspend particles typically is characterized by the yield stress. Typically, in order to stabilize the suspension particles in the liquid matrix of the liquid product, the stress applied by one single bead or particle does not exceed the yield stress of the liquid matrix. If this condition is fulfilled the liquid product will be less susceptible to sedimentation or creaming and floating or settling of the suspension particles under static conditions. The liquid matrix of the liquid detergent or personal care product of the present invention typically has a yield stress within the range of 0.003-5.0 Pa, preferably within the range of 0.01-1.0 Pa, more preferably within the range of 0.05-0.2 Importantly, although the percentages and relative amounts of the particulate cellulose material are defined herein relative to total weight of the liquid detergent or personal care product, i.e. including both liquid matrix as well as any suspended particles, the yield stress and other rheology parameters defined herein concern only the liquid matrix. The presence of suspended particles can influence yield stress measurements.

The liquid matrix of the present invention is a shear thinning fluid. Typically shear thinning, as used herein, means that liquid's resistance to flow decreases with an increasing rate of shear stress. Shear thinning can be quantified by the so called "shear thinning factor" (SF) which is obtained as the ratio of viscosity measured by Brookfield viscosimeter at 1 rpm, Bf(1), and at 10 rpm, Bf(10): A shear thinning factor below zero (SF<0) indicates shear thickening, a shear thinning factor of zero (SF=0) indicates Newtonian behavior and a shear thinning factor above zero (SF>0) stands for shear thinning behavior. In an embodiment the shear thinning property is characterized by the liquid matrix having a specific pouring viscosity, a specific low-stress viscosity, and a specific ratio of these two viscosity values. The pouring viscosity, as defined herein, is measured at a shear rate of 20 $sec^{-1}$. Suitable external structuring agents are those which provide liquid matrix having a pouring viscosity which generally ranges from 100 to 2500 cps, preferably from 100 to 1500 cps. The low-stress viscosity, as defined herein, is determined under a constant low-stress of 0.1 Pa. The liquid matrix has a low-stress viscosity of at least 1,500 cps, preferably at least 10,000 cps, and preferably at least 50,000 cps. This low-stress viscosity represents the viscosity of the liquid matrix under typically usage stress conditions and during transportation and packaging. To exhibit suitable shear-thinning characteristics, in one embodiment, the liquid matrix typically has a ratio of its low-stress viscosity to its pouring viscosity value, which is at least 2, preferably at least 10, preferably at least 100, up to 1000 or 2000.

Also, in one embodiment, the liquid matrix of the compositions of the invention have a stress v. shear rate profile with a slope of at least 0.05, preferably at at least 0.1, more preferably at least 0.2, at least 0.3, at least 0.4 or at least 0.5.

The liquid matrix of the compositions of the invention typically have a stress v. shear rate profile with a slope of below 1.5, preferably below 1, more preferably below 0.9, below 0.8, below 0.7, below 0.6 or below 0.5. More in particular, the liquid matrix of the compositions of the present invention have a stress v. shear rate profile with a slope of >0, preferably of at least 0.05, preferably at at least 0.1, more preferably at least 0.2, at least 0.3, at least 0.4 or at least 0.5, within the shear rate range of from 1 to 1000 s$^{-1}$, more preferably of 10 to 1000 s$^{-1}$, more preferably form 10 to 100 s$^{-1}$. As will be understood by those skilled in the art on the basis of the information mentioned herein, the >0 slope typically means that the product has sufficient flow stability and is less prone to shear banding and lumpiness.

Viscosity and flow behavior measurements, in accordance with this invention, are typically made using a Haake model RV550 viscometer (rotor MV1), at 1 to 1000 s$^{-1}$ and conducted at 25° C.

The liquid product of the invention can be made for any suitable cleaning purpose, including but not limited to: laundry detergent products, hand dishwashing products, machine dishwashing products, cleaning products for hard surfaces (such as lavatory fixtures, toilets, shower stalls, bathtubs, bidets, sinks, countertops, walls, floors, windows, etc.), industrial detergents, and liquid personal hygiene products, such as shampoos, conditioners, skin cleansing products and baby care products.

A further aspect of the invention concerns the use of the particulate parenchymal cellulose material as defined in any of the foregoing as a structuring agent in a liquid detergent product, especially a liquid detergent product selected from the group consisting of laundry detergent products, hand dishwashing products, machine dishwashing products, cleaning products for hard surfaces (such as lavatory fixtures, toilets, shower stalls, bathtubs, bidets, sinks, countertops, walls, floors, windows, etc.), industrial detergents, and liquid personal hygiene products, such as shampoos, conditioners, skin cleansing products and baby care products.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Examples 1

Preparation of Parenchynal Cellulose Composition Containing Particulate Cellulose Material Fresh sugar beet pulp obtained from Suikerunie Dinteloord (NL) was washed in a flotation washer in order to remove sand, pebbles, etc.

In a stirred tank (working volume 70 L) heated with steam), 16.7 kg of washed sugar beet pulp having a solids content of 15% DS (2.5 kg DS in the batch) was introduced and tap water was added to a total volume of 70 L. The mass was heated with steam and, once the temperature reached 50° C., 1200 gram NaOH is added. Heating was continued to reach a final temperature of 95° C. After 45 minutes at 95° C., the mixture was subjected to low shear for 30 minutes (using a Silverson BX with a slitted screen. After a total period of 3 hours at 95° C., low shear was applied again for 60 minutes (using the Silverson BX with an emulsor screen with apertures of 1.5 mm), during which the temperature was kept at approximately 95° C.

Reduction of the particles was done with a Gaulin high pressure homogenizer, operating at 150 bar (first stage; second stage was 0 bar). The mixture was homogenized 6 times. This step was performed at ambient temperature. The mixture had been allowed to cool to ambient temperature before being subjected to the high pressure homogenization treatment.

The homogenized mass was subsequently introduced in a mixing tank and heated to a temperature of 80-85° C., where after a microfiltration step was performed using a ceramic membrane with a pore size of 1,4 µm. The permeate was replaced with demineralized water. As soon as the conductivity of the retentate reached 1 mS/cm, microfiltration was discontinued. The dry solids content was between 0.5 and 1%.

This end-product was subsequently concentrated in a filter bag having pores of 100 µm to reach a dry solids content of 2%.

The material was analyzed using a Malvern Mastersizer, confirming a median (volume-weighted) major dimension of the particles contained within the material of 43.65 µm, with approximately 90% of the material (on the basis of volume) having a particle size of below 100 µm.

Example 2

Preparation of Parenchynal Cellulose Composition Containing Particulate Cellulose Material Fresh sugar beet pulp (320 kg, 24.1% ds) obtained from Suikerunie Dinteloord (NL) was washed in a flotation washer in order to remove sand, pebbles, etc.

The washed sugar beet pulp was transferred to a stirred tank (1000 L) and diluted to a ds concentration of 8% (800 kg). Multifect pectinase FE (Genencor, 139 units/g ds) was added and the suspension was heated to 45° C. After 48 h the suspension was pressed using a membrane filterpress (TEFSA) and the resulting solid material containing the cellulose material was isolated (216 kg 12% ds).

A portion of the resulting cellulose material (20 kg) was introduced in a stirred tank (working volume 70 L) and tap water was added to a total volume of 70 L. The mixture was heated to 95° C. and subjected to low shear for a total period of 3 hours at 95° C. (using a Silverson BX with a slitted screen. Then, low shear was applied for a further 60 minutes (using the Silverson BX with an emulsor screen with apertures of 1,5 mm), during which the temperature was kept at approximately 95° C.

Reduction of the particles was done with a Gaulin high pressure homogenizer, operating at 150 bar (first stage; second stage was 0 bar). The mixture was homogenized 6 times. This step was performed at ambient temperature. The mixture had been allowed to cool to ambient temperature before being subjected to the high pressure homogenization treatment.

The homogenized mass was subsequently introduced in a mixing tank and heated to a temperature of 80-85° C., where after a microfiltration step was performed using a ceramic membrane with a pore size of 1,4 μm. The permeate was replaced with demineralized water. As soon as the conductivity of the retentate reached 1 mS/cm, microfiltration was discontinued. The dry solids content was between 0.5 and 1%.

This end-product was subsequently concentrated in a filter bag having pores of 100 μm to reach a dry solids content of 2%.

The material was analyzed using a Malvern Mastersizer, confirming a median (volume-weighted) major dimension of the particles contained within the material of 51.03 μm, with approximately 90% of the material (on the basis of volume) having a particle size of below 100 μm.

Example 3

Preparation of 'MCF'

A new batch of particulate cellulose material of this invention was produced following the protocol of example 1. This time the end-product was concentrated to 5% dry matter content. This product is denominated 'MCF' and was used in all the subsequent experiments, some of which are described here below.

Example 4

Surfactant Viscosity Study

An experiment was conducted to evaluate the viscosity of a 0.98 wt % particulate cellulose material with a 10% active solution of various surfactants typically used in liquid laundry detergents and hand dishwashing detergents:

MCF, as obtained in example 3

SLES sample was Steol 460 from Stepan

NaDDB SA neutralized Biosoft S100 from Stepan

Samples of the control and 10% active surfactant were evaluated at t=0 and stored in an oven at 40° C. Every week the samples were stabilized to 25° C. and viscosity determined using a Brookfield Viscometer with speeds and spindle numbers indicated and then maintained at 40° C. until the next viscosity evaluation.

The results of these measurements are summarized in the following table 1. These results show that MCF forms stable mixtures with SLES and Sodium salt of dodecylbenzene sulphonate. Synergetic viscosity build-up takes place with Sodium salt of dodecylbenzene sulphonate. Under these storage conditions a 6 week stability could indicate a 1 year self stability.

TABLE 1

| Viscosity in mPa · s | Spindle | t = 0 | 1 wk | 2 wks | 3 wks | 5 wks | 7.5 wks |
|---|---|---|---|---|---|---|---|
| 0.98 wt % MCF with water (control) | 2@30 rpm | 250 | 255 | 250 | 250* | 250* | 250* |
| 0.98 wt % MCF + 10% SLES (balance water) | 2@30 rpm | 370 | 360 | 360 | 360 | 360 | 360 |
| 0.98 wt % MCF + 10% NaDDBSA (balance water) | 2@12 rpm | 9.700 | 9.70 | 9.500 | 17.000** | 16.800** | 15.800** |

*Some phase separation observed.
**Changed to spindle 3@6 rpm due to increased viscosity.

Example 5

Surfactant+Builder Viscosity Study

An experiment was conducted to evaluate the viscosity of a solution of 0.5 wt % MCF with combinations of surfactants and builders typically used in liquid laundry detergents and hand dishwashing detergents:

Mixtures of 0.5% active MCF+3 to 10% sodium dodecyl benzene sulphonic acid+3 to 7% alcohol ethoxylate+ (optional) 5% citrate or soda ash were tested.

Control sample (0.5% active Betafib in water)=1000 mPa·s

Samples were evaluated at t=0 and stored in a oven at 35° Celsius. At intervals of approx. one week the samples were stabilized to 25° C. and viscosity determined using a Brookfield Viscometer. Samples are maintained at 35° C. until the next viscosity evaluation.

The results of these measurements are summarized in the following table 2. These results show no significant difference in viscosity t=0, 1 week, 2 weeks and 4 weeks (unless indicated otherwise). These results give rise to the following conclusions:

Higher ratios of Na-DDB SA resulted in more stable product.

Increasing the ratio of Na-DDBSA resulted in higher viscosity.

Both soda ash and citrate assisted in increasing the overall viscosity of surfactant blends.

Both soda ash and citrate assisted in providing better stability for the surfactant blends that were initially unstable (e.g. low Na-DDBSA/high AE).

TABLE 2

| 0.5% active MCF | 10% Na-DDBSA | 7% Na-DDBSA + 3% AE | 5% Na-DDBSA + 5% AE | 3% Na-DDBSA + 7% AE |
|---|---|---|---|---|
| No builder | 1400 mPa·s | 1400 mPa·s | 800 mPa·s | 600 mPa·s |
| 5% soda ash | 3000 mPa·s | 2000 mPa·s | 1400 mPa·s | 1400 mPa·s |
| 5% citrate | 2900 mPa·s | 2000 mPa·s | 2000 mPa·s | 1400* mPa·s |

*initial viscosity 1800 cps

Remark:
Some phase separation was seen initially and after 1 week with 5% Na-DDBSA + 5% AE and 3% Na-DDBSA + 7% AE. However, after 2 weeks the mixtures were homogenous.

Example 6

Stability of MCF in the Presence of Electrolytes and Builders

Samples of MCF were mixed with DI water with the following ratio 6000 ml of DI water with 400 grams of MCF under high shear for 30 minutes. Samples were allowed to stabilize for 2 hours and were then mixed under low sheer for 15 minutes. The solutions would represent a 6.26% solution of MCF, or 0.9375% on a dry basis at 15 w/w of dry matter.

Samples were challenged for accelerated stability by storing in oven at 35 C, temperature for measuring viscosity were measured at 25 C by placing then in a water bath for a couple of hours until this temperature was reached.

The following electrolytes/builders were studies at the following concentrations:

Sodium Citrate, Sodium sulphate, Sodium Metasilicate Pentabead, Sodium carbonate (soda ash dense), Sodium Chloride, Citric acid, Magnesium Sulphate.

%, 1.0%, 2.0%, 5.0%

Control: Viscosity without electrolytes 1,800—this viscosity has remained very constant at 1,800 cps.

The results of these measurements are summarized in the following tables 3 and 4 (measurements in mPa·s measured using a Brookfield Viscometer, all measurements are at 25 C and measured in mPa·s). These results give rise to the following conclusions:

The addition of electrolytes/builders increases the viscosity of the MCF.

The results indicate that viscosity of the MCF is not negatively affected by the level of electrolyte/builder. This is very different to most structurants.

An important observation noted is that in no samples were any phase separation even after 6 weeks of oven storage at 35 Celcius. At 6 weeks there was slight changes in viscosity but nothing that would indicate a trend towards significant viscosity loss or significant viscosity gain-generally indicating that MCF is relatively stable to the electrolyte/builders examined.

The results are very interesting in that they demonstrate MCF is remarkably stable in a variety of electrolyte/builder systems—which are very different chemically.

TABLE 3

After 24 hours using spindle 3 at 30 rpm

| Chemical | 0.1% | 1.0% | 2.0% | 5.0% |
|---|---|---|---|---|
| Sodium Citrate | 2,600 | 2,600 | 2,800 | 3,200 |
| Sodium metasilicate | 2,400 | 2,200 | 2,000 | 2,400 |
| Magnesium Sulphate | 2,000 | 2,200 | sample issue | 2,200 |
| Sodium chloride | 2,800 | 2,000 | 2,800 | 2,800 |

TABLE 3-continued

After 24 hours using spindle 3 at 30 rpm

| Chemical | 0.1% | 1.0% | 2.0% | 5.0% |
|---|---|---|---|---|
| Citric acid | 2,200 | 2,400 | 2,200 | 2,200 |
| Sodium sulphate | 2,800 | 2,800 | 2,800 | 2,800 |
| Sodium carbonate | 2,400 | 2,400 | 2,600 | 2,400 |

TABLE 4

After 6 weeks using spindle 3 at 30 rpm

| Chemical | 0.1% | 1.0% | 2.0% | 5.0% |
|---|---|---|---|---|
| Sodium Citrate | 2,800 | 2,800 | 2,800 | 3,000 |
| Sodium metasilicate | 2,600 | 2,600 | 2,400 | 2,400 |
| Magnesium Sulphate | 2,200 | 2,200 | Sample issue | 2,200 |
| Sodium chloride | 2,600 | 2,400 | 2,800 | 2,600 |
| Citric acid | 2,400 | 2,400 | 2,400 | 2,400 |
| Sodium sulphate | 2,600 | 2,600 | 2,600 | 2,800 |
| Sodium carbonate | 2,600 | 2,200 | 2,200 | 2,400 |

Example 7

Stress-shear Rate Profile

FIG. 1a shows the stress vs. shear rate profile of a 0.5% (w/w) MCF in water system. The measurements were made using using a Haake model RV550 viscometer (rotor MV1), at 1 to 1000 s$^{-1}$ and conducted at 25° C. As can be inferred from this profile the slope is >>0, which is indicative of sufficient flow stability.

Figure 1B:
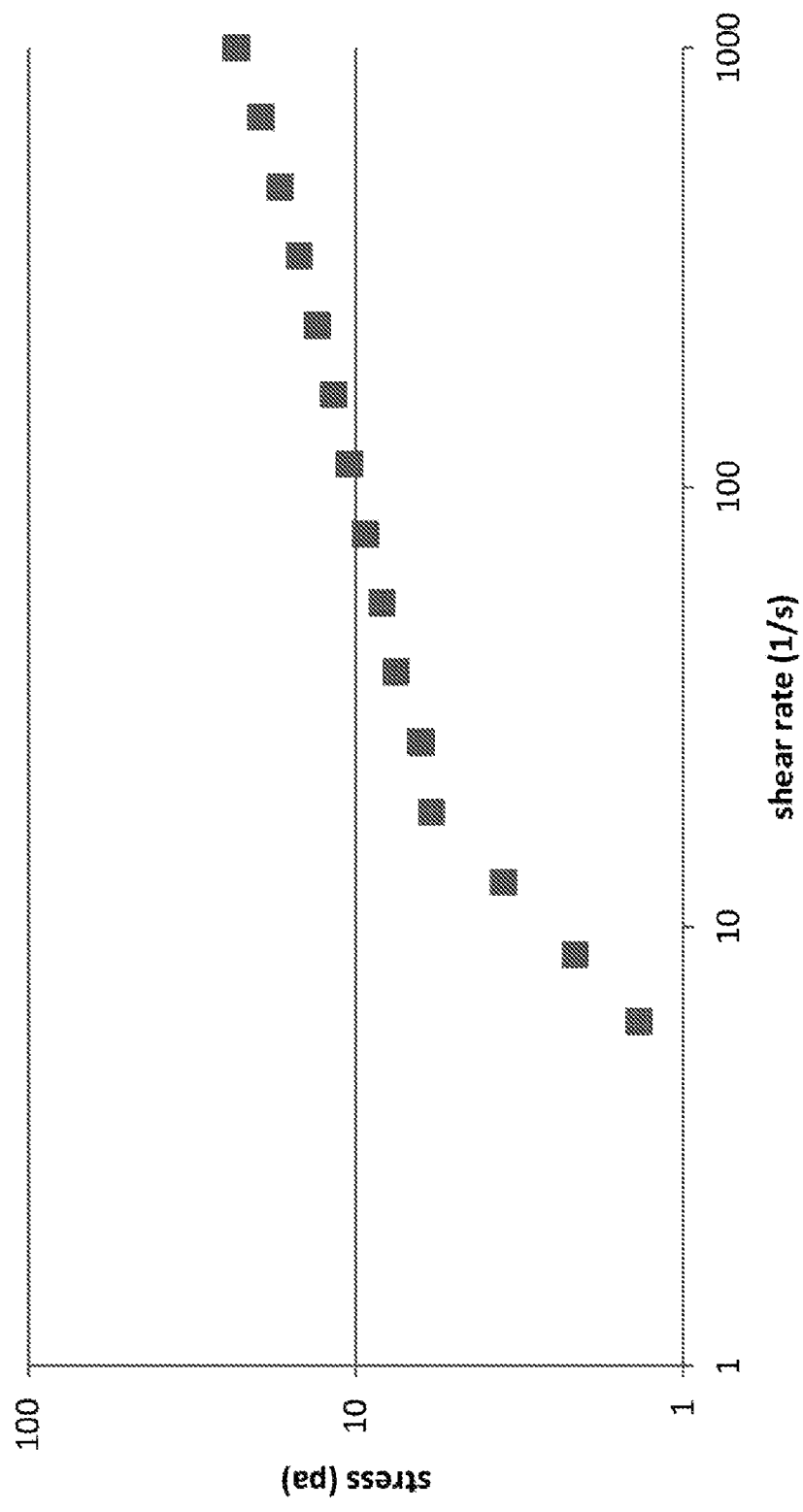
Figure 1b shows the stress vs. shear rate profile of a 1.0% (w/w) MCF in water system.

FIG. 1b shows the stress vs. shear rate profile of a 1.0% (w/w) MCF in water system. The measurements were made using using a Haake model RV550 viscometer (rotor MV1), at 1 to 1000 s$^{-1}$ and conducted at 25° C. As can be inferred from this profile the slope is >>0, which is indicative of sufficient flow stability.

Example 8

Effect of pH on Viscosity

Figure 2:
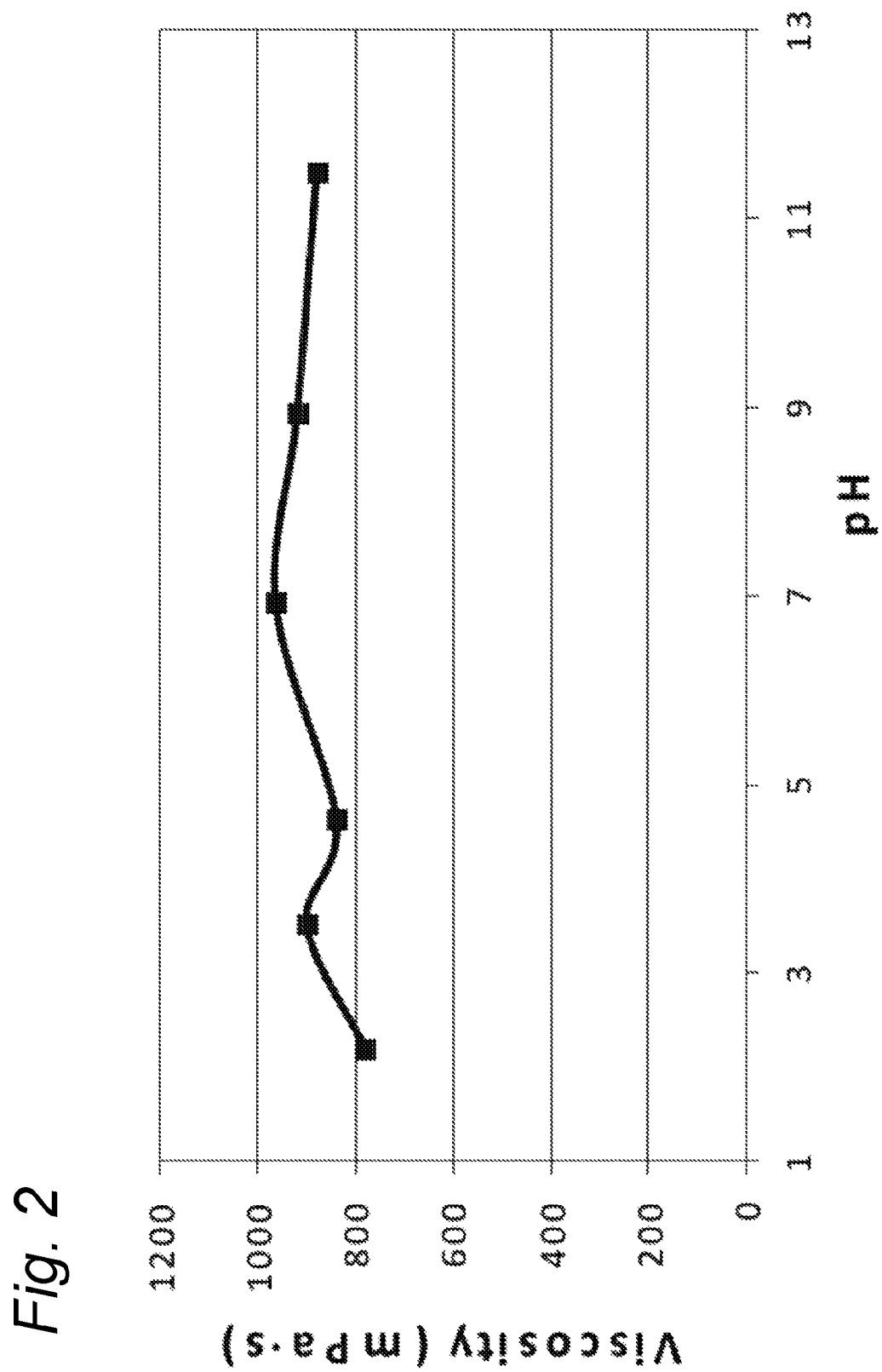
FIG. 2 shows the viscosity vs. pH profile of a 0.6% (w/w) MCF in water system, the pH of which was adjusted using NaOH and HCl.

FIG. 2 shows the viscosity vs. pH profile of a 0.6% (w/w) MCF in water system, the pH of which was adjusted using NaOH and HCl. The measurements were made using a Haake model RV550 viscometer (rotor MV1), at 1 to 1000 s$^{-1}$ and conducted at 25° C. As can be inferred from this profile the viscosity is hardly affected by the pH value of the system.

Example 9

Effect of HCl on Stability

Figure 3A:
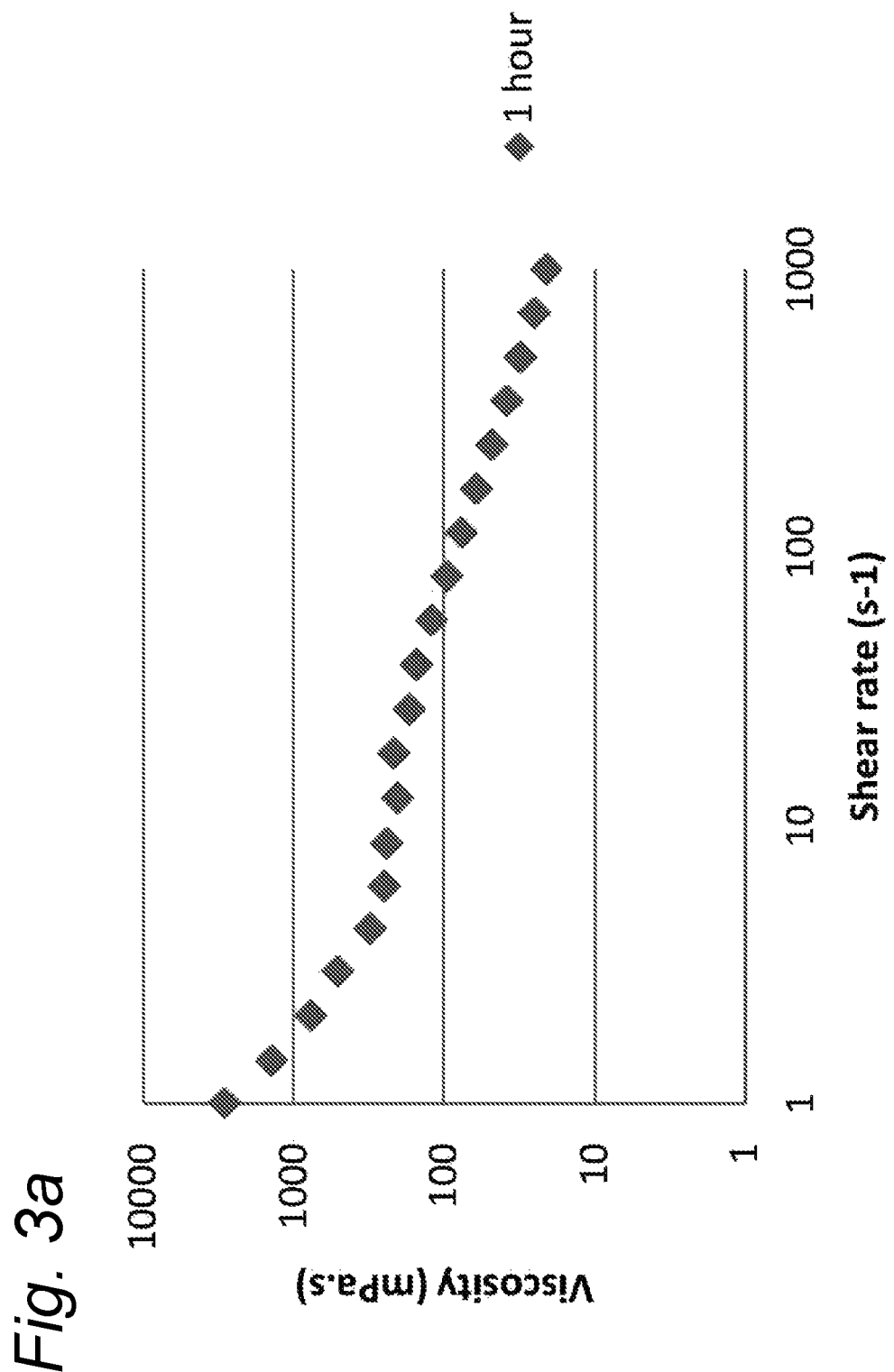
FIGS. 3a, 3b and 3c show the shear rate vs. viscosity profile of a 1% (w/w) MCF in water system, containing 9% (w/w) HCl, after 1 hour, 24 hours and 48 hours respectively.
Figure 3B:
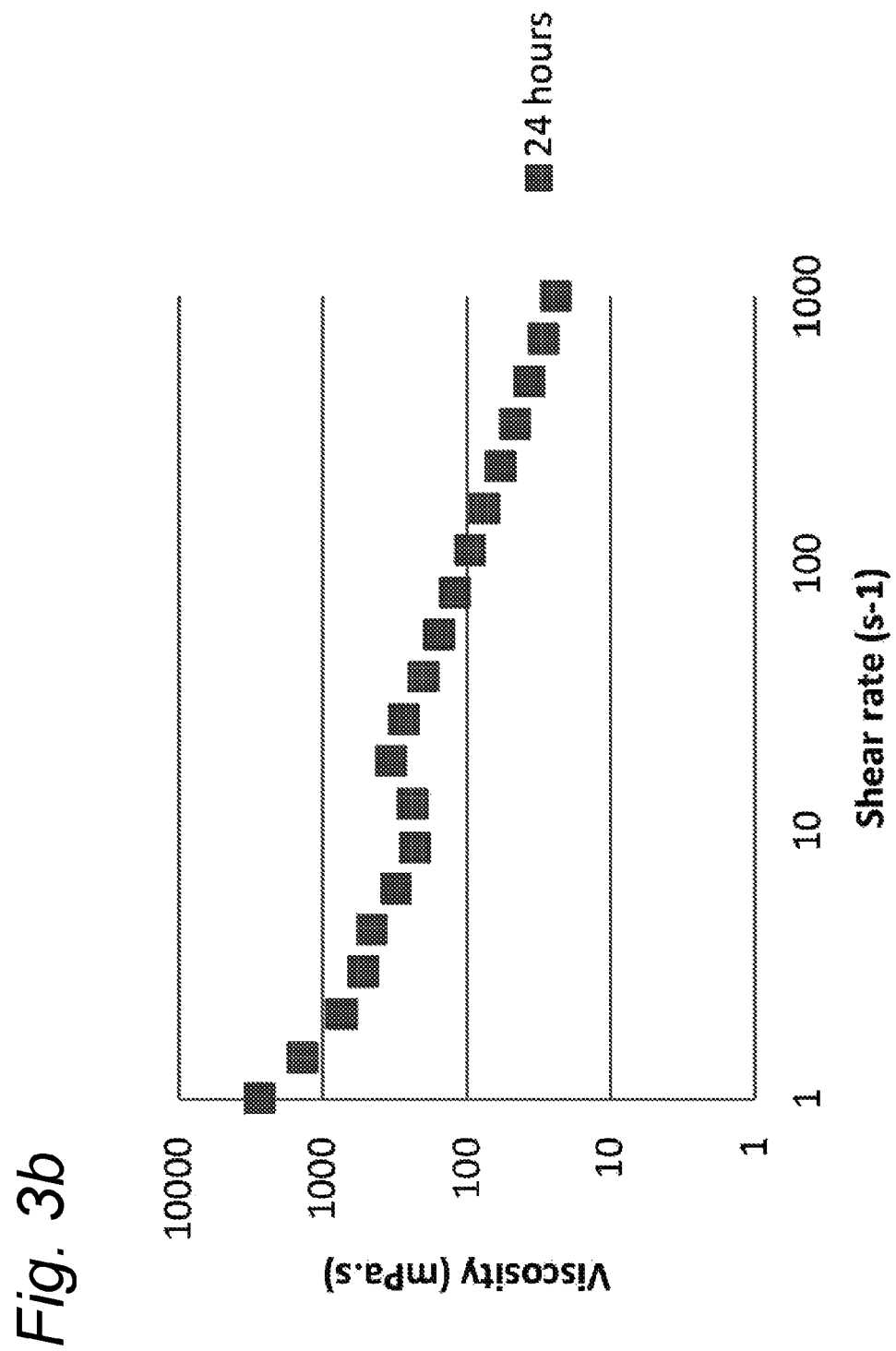
Figure 3C:
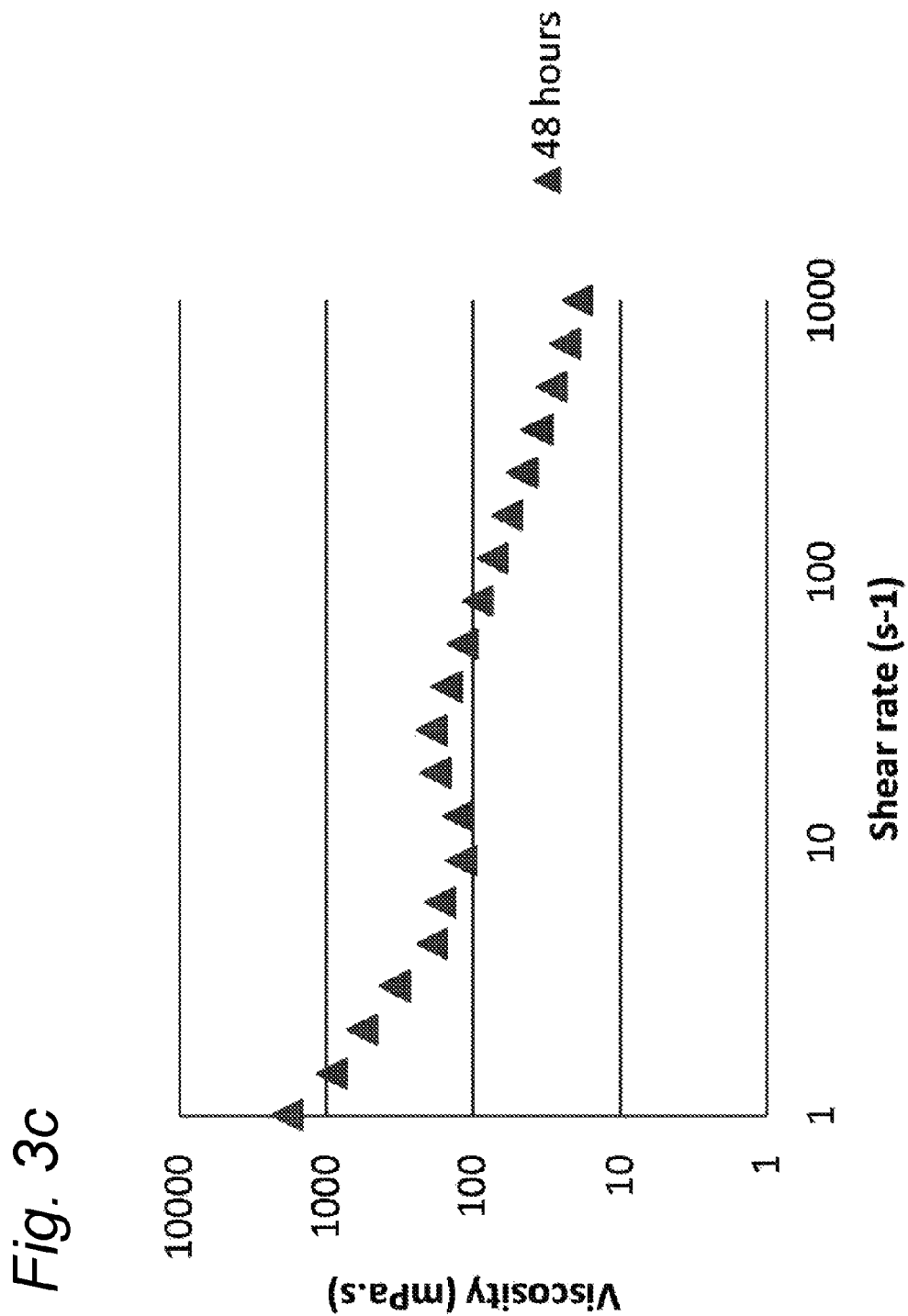

FIGS. 3a, 3b and 3c show the shear rate vs. viscosity profile of a 1% (w/w) MCF in water system, containing 9% (w/w) HCl, after 1 hour, 24 hours and 48 hours respectively. The measurements were made using a Haake model RV550 viscometer (rotor MV1), at 1 to 1000 s$^{-1}$ and conducted at 25° C. As can be inferred from these figures the profile did not substantially change over the 48 hour test period. This is indicative of the stability of the structuring agent of the present invention in extremely acidic systems.

Example 10

Effect of CaCO$_3$ Particles on Viscosity

Figure 4:
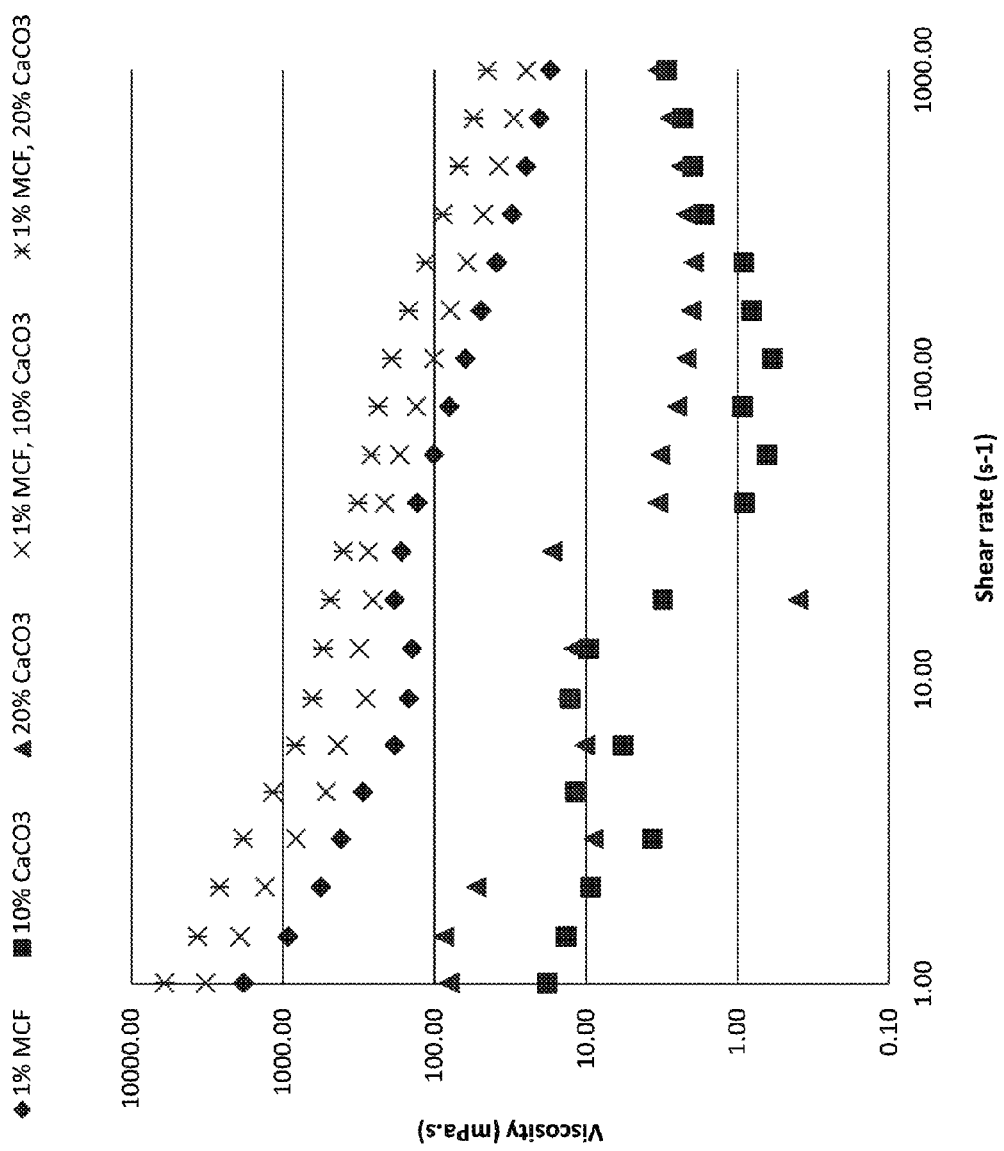
FIG. 4 shows the shear rate vs. viscosity profile of several MCF structured systems and control samples as identified.

FIG. 4 shows the shear rate vs. viscosity profile of the following MCF structured systems and control samples:
- 1% (w/w) MCF in tap water
- 10% (w/w) CaCO$_3$ in tap water
- 20% (w/w) CaCO$_3$ in tap water
- 1% (w/w) MCF+10% (w/w) CaCO$_3$ in tap water
- 1% (w/w) MCF+20% (w/w) CaCO$_3$ in tap water The measurements were made using a Haake model RV550 viscometer (rotor MV1), at 1 to 1000 s$^{-1}$ and conducted at 25° C. As can be inferred from this figure, the presence of particles of non-soluble material (CaCO$_3$) does not substantially change the profile. The presence of such particles slightly increases the viscosity of the system.

Example 11

Effect of Bleaching on Viscosity

Figure 5:
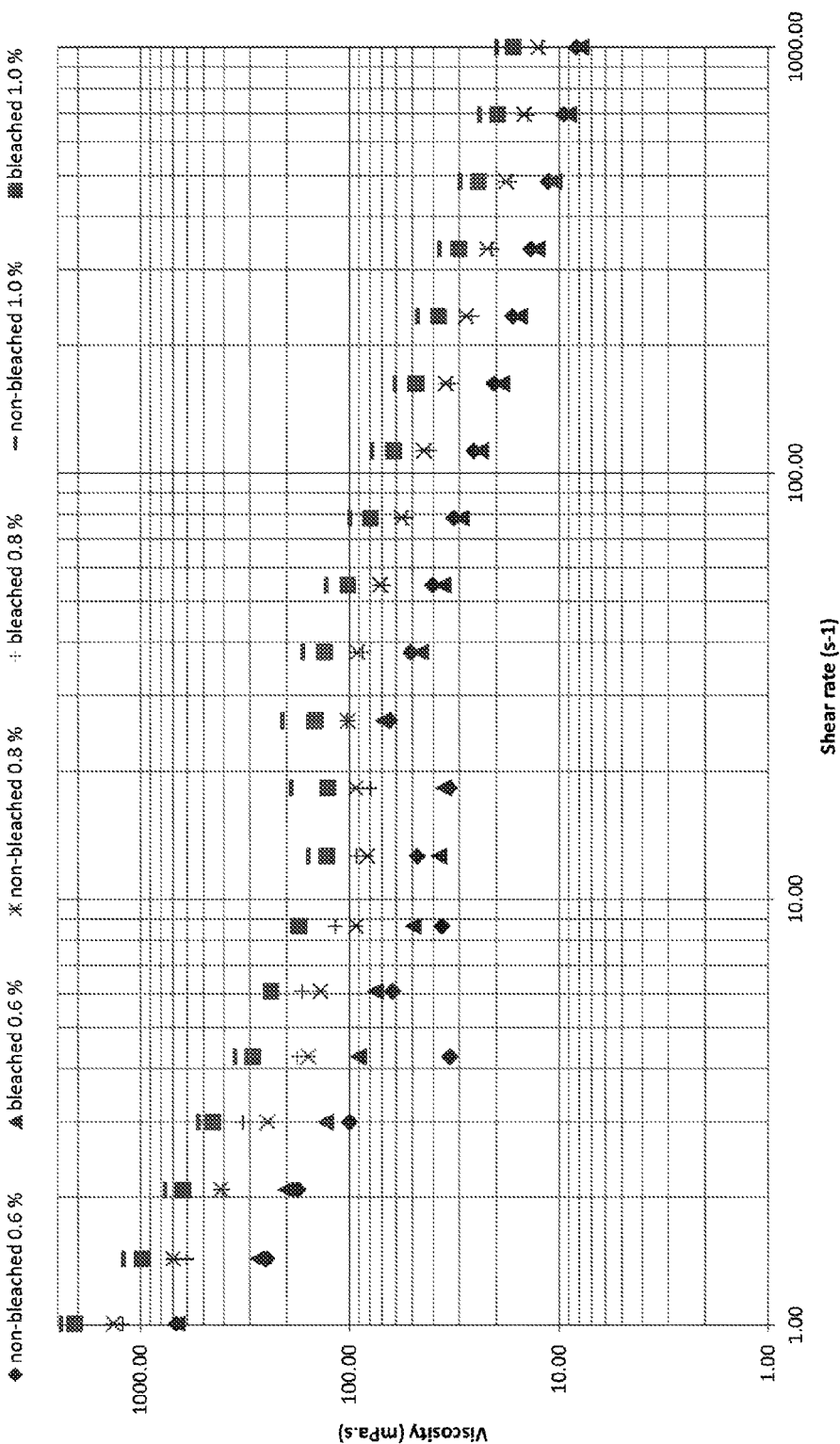
FIG. 5 shows the shear rate vs. viscosity profile of additional MCF structured systems and control samples as identified.

An amount of MCF was subjected to treatment with sodium silicate, diethylene triamine pentaacetic acid (DTPA) and H$_2$O$_2$ (pH adjustment with NaOH and H$_2$SO$_4$), which resulted (after washing) in a product with improved visual appearance. FIG. 5 shows the shear rate vs. viscosity profile of the following MCF structured systems and control samples:
- 0.6% (w/w) MCF in tap water
- 0.6% (w/w) bleached MCF in tap water
- 0.8% (w/w) MCF in tap water
- 0.8% (w/w) bleached MCF in tap water
- 1.0% (w/w) MCF in tap water
- 1.0% (w/w) bleached MCF in tap water The measurements were made using a Haake model RV550 viscometer (rotor MV1), at 1 to 1000 s$^{-1}$ and conducted at 25° C. As can be inferred from this figure, applying a bleaching step to improve the visual appearance of the structuring agent of the invention does not substantially change the profile.

The invention claimed is:

1. A liquid product selected from the group consisting of laundry detergent products, hand dishwashing products, machine dishwashing products, cleaning products for hard surfaces, and personal hygiene products, comprising:
   (a) an aqueous medium;
   (b) 5-70% by weight of a surfactant system; and
   (c) an external structuring agent;
   wherein the external structuring agent comprises particulate parenchymal cellulose material comprising, by dry weight of the particulate cellulose material, (i) at least 70% cellulose, (ii) 0.5-10% pectin and (iii) 1-15% hemicellulose, wherein the particulate cellulose material has a volume-weighted median major dimension between 25-75 μm and wherein at least 90%, on a volume basis, of the particles have a diameter less than 120 μm, when measured with a Malvern Mastersizer particle size analyzer.

2. The liquid product according to claim 1, wherein the particulate material has a volume-weighted median major particle dimension within the range of 35-65 μm, as measured by laser light diffractometry.

3. The liquid product according to claim 1, wherein the particulate cellulose material is obtainable by:
   (a) subjecting a parenchyma cell-containing vegetable pulp to chemical and/or enzymatic treatment resulting in partial degradation and/or extraction of pectin and hemicellulose; and
   (b) subjecting the material of (a) to a high shear process, wherein the particle size of the cellulose material is reduced.

4. The liquid product according to claim 1, wherein the particulate cellulose material is derived from sugar beet pulp.

5. The liquid product according to claim 1, wherein the particulate cellulose material comprises, by dry weight of the particulate cellulose material, less than 5% pectin.

6. The liquid product according to claim 5, wherein the particulate cellulose material comprises, by dry weight of the particulate cellulose material, less than 2.5% pectin.

7. The liquid product according to claim 1, wherein the particulate cellulose material comprises, by dry weight of the particulate cellulose material, 5-15% of hemicellulose.

8. The liquid product according to claim 7, wherein the particulate cellulose material comprises, by dry weight of the particulate cellulose material, 5-10% of hemicellulose.

9. The liquid product according to claim 1, wherein the morphology of the particulate cellulose material has cellulose network structures.

10. The liquid product according to claim 1, comprising less than 10 wt. % of unraveled cellulose nanofibrils.

11. The liquid product according to claim 1, comprising: (a) an aqueous medium; (b) 0.1-70% (w/w) of the surfactant system, and (c) 0.01-5% (w/w) of the external structuring agent.

12. The liquid product according to claim 1, comprising less than 0.05 wt. % of bacterial cellulose.

13. The liquid product according to claim 1, wherein the product is a concentrated product comprising 1 to 30% (w/w) water.

14. The liquid product according to claim 1, wherein the product is a concentrated product comprising 5 to 15% (w/w) water.

15. The liquid product according to claim 1, wherein the composition has slope of stress (on y axis, measured in pascals) versus shear rate (on x axis, measured in s$^{-1}$) of 0.05 to 0.75.

16. The liquid product according to claim 1, further comprising (d) up to 25% (w/w) of one or more adjunct ingredients.

17. The liquid product according to claim 1, wherein at least 90%, on a volume basis, of the particles have a diameter less than 110 μm.

18. The liquid product according to claim 17, wherein at least 90%, on a volume basis, of the particles have a diameter less than 100 μm.

19. The liquid product according to claim 1, wherein the surfactant system comprises a cationic surfactant.

20. The liquid product according to claim 1, wherein the surfactant system comprises an anionic surfactant.

21. The liquid product according to claim 1, wherein the surfactant system comprises a non-ionic surfactant.

22. A method of preparing a liquid product according to claim 1, the method comprising:
  (a) subjecting parenchymal cell-containing vegetable pulp to chemical and/or enzymatic treatment resulting in partial degradation and/or extraction of pectin and hemicellulose, wherein the mixture may be homogenized once or several times by applying low shear force during and/or after said chemical and/or enzymatic treatment;
  (b) subjecting the material resulting from step (a) to a high shear process, wherein the particle size of the cellulose material is reduced so as to yield a particulate material having a volume-weighted median major dimension within the range of 25-75 μm, and wherein at least 90%, on a volume basis, of the particles have a diameter less than 120 μm, as measured by laser diffractiometry; and
  (c) removing liquid from the mass obtained in step (b) and adding an aqueous medium and a surfactant system.

23. The liquid or personal care product according to claim 1, wherein the liquid personal hygiene products are selected from the group consisting of conditioners, skin cleansing products and baby care products.

* * * * *